(12) United States Patent
Bonner-Weir et al.

(10) Patent No.: US 6,815,203 B1
(45) Date of Patent: Nov. 9, 2004

(54) METHODS OF MAKING PANCREATIC ISLET CELLS

(75) Inventors: Susan Bonner-Weir, Cambridge, MA (US); Monica Taneja, Bronx, NY (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 09/602,508

(22) Filed: Jun. 23, 2000

Related U.S. Application Data

(60) Provisional application No. 60/140,639, filed on Jun. 23, 1999.

(51) Int. Cl.[7] .............................. C12N 5/06; C12N 5/08
(52) U.S. Cl. ...................... 435/377; 435/375; 435/384; 435/366; 435/370
(58) Field of Search ................................. 435/377, 375, 435/384, 366, 370, 325

(56) References Cited

U.S. PATENT DOCUMENTS

| | | | |
|---|---|---|---|
| 4,439,521 A | | 3/1984 | Archer et al. ................... 435/1 |
| 4,829,000 A | * | 5/1989 | Kleiman et al. ........ 435/240.23 |
| 4,935,000 A | * | 6/1990 | Dudek .......................... 600/36 |
| 5,681,587 A | | 10/1997 | Halberstadt et al. ......... 424/562 |
| 5,888,705 A | | 3/1999 | Rubin et al. ................ 435/366 |
| 6,077,692 A | | 6/2000 | Ruben et al. |
| 6,326,201 B1 | | 12/2001 | Fung et al. |

FOREIGN PATENT DOCUMENTS

| | | |
|---|---|---|
| WO | WO 96 40872 | 12/1996 |
| WO | WO 02 29010 | 4/2002 |

OTHER PUBLICATIONS

Kerr–Conte et al. Diabetes. 1996. vol. 45, pp. 1108–1114.*
Rawdon B.B. Microsc. Res. Tech. 1998. vol. 43, pp. 292–305.*
Hayek et al., "Growth Factor/Matrix–Induced . . . ," Diabetes, 44:1458–1460, 1995.
Bonner–Weir et al., "Islet Cell Growth and the Growth . . . ," TEM, 5(2):60–64, 1994.
Beattie et al., "Regulation of Proliferation and . . . ," Diabetes, 45:1223–1228, 1996.
Carlsson et al. Endocrimology, (1997) vol. 138, No. 9, pp. 3940–3948.
Gmyr et al., "Expansion of Human Ductal Pancreatic Stem Cells . . .", 1997, Acta Diabetological, Springer International, Berlin, DE, 34(2);107.
Kerr–Conte.et al., "Model for Human Islet Neogenesis in Vitro . . .", 1995, Transplantation Proceedings, 27(6);3268.
Kerr–Conte et al., "Model for Islet Cell Neogenesis from Adult Human . . .", 1997, Experimental and Clinical Endocrinology and Diabetes, 105(4);A28–A29.
L. Rosenberg, "In Vivo Cell Transformation: Neogenesis of Beta . . .", 1995, Cell Transplantation, Elsevier Science, US, 4(4);371–383.
Wang et al., "Pancreatic Duct Cells Express Gastrin . . .", 1996, Diabetological, Berlin, DE, 39(suppl 1);A63.
Yuan et al., "Transdifferentiation of human islets to pancreatic . . .", 1996, Differentiation, Springer Verlag, DE, 61(1);67–75.
Bonner–Weir et al., "Partial Pancreatectomy as a Model of Pancreatic Regeneration", 1997,Pancreatic Growth and Regeneration;138–153.

* cited by examiner

*Primary Examiner*—Vera Afremova
(74) *Attorney, Agent, or Firm*—Fish & Richardson P.C.

(57) ABSTRACT

The invention features methods of promoting dedifferentiation of pancreatic cells, methods of obtaining pancreatic islet cells from the dedifferentiated pancreatic cells, and methods of treating a subject having a disorder characterized by insufficient pancreatic islet function by administering pancreatic islet cells obtained by these methods.

36 Claims, 3 Drawing Sheets

SEQUENCE LISTING

```
<160> NUMBER OF SEQ ID NOS: 8

<210> SEQ ID NO 1
<211> LENGTH: 19
<212> TYPE: DNA
<213> ORGANISM: Homo sapiens

<400> SEQUENCE: 1
tcacacctgg tggaagctc                                                      19

<210> SEQ ID NO 2
<211> LENGTH: 18
<212> TYPE: DNA
<213> ORGANISM: Homo sapiens

<400> SEQUENCE: 2
acaatgccac gcttctgc                                                       18

<210> SEQ ID NO 3
<211> LENGTH: 18
<212> TYPE: DNA
<213> ORGANISM: Artificial Sequence
<220> FEATURE:
<223> OTHER INFORMATION: primer for PCR

<400> SEQUENCE: 3
atgaacgagg acaagcgc                                                       18

<210> SEQ ID NO 4
<211> LENGTH: 18
<212> TYPE: DNA
<213> ORGANISM: Artificial Sequence
<220> FEATURE:
<223> OTHER INFORMATION: primer for PCR
```

```
-continued

<400> SEQUENCE: 4
ttcaccagcc aagcaatg                                                    18

<210> SEQ ID NO 5
<211> LENGTH: 18
<212> TYPE: DNA
<213> ORGANISM: Artificial Sequence
<220> FEATURE:
<223> OTHER INFORMATION: primer for PCR

<400> SEQUENCE: 5
cccaccgtgt tcttcgac                                                    18

<210> SEQ ID NO 6
<211> LENGTH: 19
<212> TYPE: DNA
<213> ORGANISM: Artificial Sequence
<220> FEATURE:
<223> OTHER INFORMATION: primer for PCR

<400> SEQUENCE: 6
atcttctgct ggtcttgcc                                                   19

<210> SEQ ID NO 7
<211> LENGTH: 22
<212> TYPE: DNA
<213> ORGANISM: Artificial Sequence
<220> FEATURE:
<223> OTHER INFORMATION: primer for PCR

<400> SEQUENCE: 7
ccttgtgctg gcagtccttt cc                                               22

<210> SEQ ID NO 8
<211> LENGTH: 23
<212> TYPE: DNA
<213> ORGANISM: Artificial Sequence
<220> FEATURE:
<223> OTHER INFORMATION: primer for PCR

<400> SEQUENCE: 8
tctgtgaggc tgacaatgtc tgc                                              23
```

METHODS OF MAKING PANCREATIC ISLET CELLS

This application claims the benefit of prior U.S. provisional application 60/140,639, filed Jun. 23, 1999.

GOVERNMENT RIGHTS

This invention was made with support from the U.S. government under grant number NIH DK 44523 awarded by the National Institutes of Health. The government has certain rights in the invention.

BACKGROUND OF THE INVENTION

The term "idiopathic diabetes mellitus" covers a heterologous group of disorders having common symptomatic characteristics. These symptoms include an absolute or relative insulin deficiency, fasting hyperglycemia, glycosuria and a tendency to develop arteriosclerosis, neuropathy and nephropathy. At least two major as well as several less common variants of the disease have been identified. One of the major types of diabetes is insulin-dependent diabetes mellitus (IDDM) or Type 1 diabetes which covers about 10% of patients having diabetes. The other major type of diabetes, non-insulin dependent diabetes mellitus (NIDDM) or Type 2 diabetes, represents the remaining 90% of patients having diabetes.

Absent regular insulin replacement therapy using exogenously produced insulin and/or careful monitoring of diet, diabetes patients experience a wide range of debilitating symptoms, which can progress to coma and ultimately death.

An alternative method of treating diabetes which does not require repeated administration of insulin and/or strict monitoring of diet is the transplantation of pancreatic cells or tissue from a donor to a diabetic patient. However, a major problem with pancreatic cell tissue transplantation is the shortage of human donor tissue. Only about 3,000 cadaver pancreases become available in the United States each year while about 35,000 new cases of Type 1 diabetes are diagnosed each year. Hering et al. (1999) Graft 2:12–27.

SUMMARY OF THE INVENTION

The present invention is based, in part, on the discovery that pancreatic duct and exocrine cells are capable of serving as precursor cells. It was found that by replication, mature duct and/or exocrine cells can revert to a less differentiated cell that can then redifferentiate into islet, exocrine or mature duct cells and that external signals direct the phenotypic differentiation of these cells. Thus, pancreatic duct cells can provide a source of islet cells which can be used in transplantation procedures.

Accordingly, in one aspect, the invention features a method of promoting dedifferentiation of pancreatic cells. The method includes: obtaining a population of adult or differentiated pancreatic cells; and allowing the adult or differentiated cells to proliferate, e.g., rapidly proliferate, e.g., proliferate in the presence of an agent which promotes expansion., thereby providing dedifferentiated pancreatic cells.

In a preferred embodiment, the population of adult or differentiated pancreatic cells can be: a population substantially free of islet cells, e.g., a population from which the islet cells have been removed or have been substantially removed. In a preferred embodiment, the pancreatic cells are human pancreatic cells. In a preferred embodiment, the population of cells includes: duct cells; exocrine cells; duct and exocrine cells; less than about 60%, 50%, 40%, 30%, 20%, 10%, 5%, 1% islet cells. In a preferred embodiment, the population of cells is obtained form cells remaining after islet isolation.

In a preferred embodiment, the population of cells is selected based on the ability to attach to a container, e.g., a culture flask, e.g., a non-sticky culture flask. These cells are also referred to herein as "adherent cells". In another preferred embodiment, the cells that do not attach to the container are removed from the container and cultured in another container until until the cells attach. Preferably, the cells that do not attach to the container are removed when at least 1%, 2%, 3%, 5%, 10%, 15%, 20% or more of the surface of the container has cells attached to it. Once the cells attach, they can be used in the methods of the invention. In a preferred embodiment, the adherent cells express low levels or no insulin, e.g., the cells express less than about 600 ng, 500 ng, 400 ng, 300 ng, 200 ng, 150 ng, 100 ng, 50 ng of insulin. In a preferred embodiment, the adherent cells have: less than about 50%, 45%, 40%, 35%, 30%, 25%, 20%, 15%, 10%, 5%, 3%, 2%, 1% the insulin content of an original sample of cells obtained from a pancreas or pancreases; less than about 50%, 45%, 40%, 35%, 30%, 25%, 20%, 15%, 10%, 5%, 3%, 2%, 1% the DNA content of an original sample of cells obtained from a pancreas or pancreases.

In a preferred embodiment, the agent which promotes expansion is: a polypeptide or fragment or analog thereof which binds TGF-$\beta$, e.g., a soluble TGF-$\beta$ receptor; an antibody which binds TGF-$\beta$; an nucleic acid which binds to TGF-$\beta$ and inhibits TGF-$\beta$ expression, e.g., a TGF-$\beta$ antisense molecule; at least one growth factor; combinations thereof.

In a preferred embodiment, the method includes providing an agent which promotes proliferation of adult or differentiated pancreatic cells. Preferably, the agent is a growth factor or a combination of growth factors. The growth factor can be one or more of: keratinocyte growth factor (KGF); epidermal growth factor (EGF); transforming growth factors (TGF-$\alpha$); hepatocyte growth factor (HGF). Preferably, the growth factor is KGF.

In a preferred embodiment, the cells are allowed to proliferate by placing the cells on a substrate, e.g., a container, e.g., a plastic container, with medium containing an agent which promotes proliferation of adult or differentiated pancreatic cells, e.g., a growth factor, e.g., KGF, EGF, TGF-$\alpha$, and/or HGF. In a preferred embodiment, the growth factor is a growth factor which promotes the proliferation of pancreatic duct cells, e.g., rapid proliferation of pancreatic duct cells.

In a preferred embodiment, the container is: a plastic container, e.g., a plastic flask, e.g., a non-sticky plastic flask; a plastic container wherein an extracellular matrix protein has been laid down in the container, e.g., plastic container, e.g., plastic flask. In a preferred embodiment, the extracellular matrix protein is laid down by a cell, e.g., the extracellular matrix is laid down by a cancer derived cell line, e.g., a bladder carcinoma cell line, e.g., an A431 cell line. In another preferred embodiment, the extracellular matrix protein is: added to the container; is a laminin, e.g., laminin 5; is a collagen, e.g., collagen I and/or collagen IV.

In a preferred embodiment, the cells are placed on a substrate in a glucose-containing media, e.g., the glucose-containing media comprises about 4 mM, 6 mM, 8 mM, 10 mM glucose. The media can be serum free. In a preferred embodiment, nicotinamide is added to the media; insulin/transferrin/selenium (ITS) is added to the media; bovine serum albumin (BSA) is added to the media; combinations of nicotinamide, ITS and/or BSA is added to the media.

In a preferred embodiment, the population of cells is: cultured until confluent; cultured until semi-confluent; cultured until the cells form a monolayer. In a preferred embodiment, the population of cells is cultured until at least about 40%, 50%, 60%, 70%, 75%, 80%, 85%, 90%, 95% confluency.

In a preferred embodiment, the population of cells is cultured for at least 1, 2, 3, 5, 10, 14, 18, 20, 25, 30 or more days.

In a preferred embodiment, the dedifferentiated pancreatic cells express a marker indicative of expansion. The marker can be one or more of: cytokeratin; PDX-1; IPF-1; Pref-1; lack of insulin.

In another aspect, the invention features a method of obtaining pancreatic islet cells from dedifferentiated pancreatic cells. The method includes adding an extracellular matrix component to a population of dedifferentiated pancreatic cells; and culturing the cells, to thereby obtaining pancreatic islet cells.

In a preferred embodiment, the population of dedifferentiated cells includes: dedifferentiated duct cells; dedifferentiated exocrine cells; both dedifferentiated duct cells and dedifferentiated exocrine cells. In a preferred embodiment, the cells are human cells.

In a preferred embodiment, the population of cells: is a monolayer of cells; has been cultured until semi-confluent; has been cultured until confluent. In a preferred embodiment, Lp; the population of cells has been cultured until at least about 40%, 50%, 60%, 70%, 75%, 80%, 85%, 90%, 95% confluency.

In a preferred embodiment, the dedifferentiated pancreatic cells express a marker indicative of expansion. The marker can be one or more of: cytokeratin; IPF-1; Pref-1; lack of insulin.

In a preferred embodiment, the extracellular matrix component is one or more of: laminin, e.g., laminin 1; collagen, e.g., collagen IV; entactin; heparin sulfate proteoglycan; nidogen. In a preferred embodiment, the extracellular matrix component is a basement membrane derived substance, e.g., a basement membrane laid down by a cell, e.g., a tumor cell, e.g., an Engelbreth-Holm-Swarm (EHS) tumor cell. Preferably, the extracellular matrix component is Matrigel™. In a preferred embodiment, the extracellular component further includes: one or more growth factor(s); one or more matrix metalloproteinase(s) (MMP), e.g., MMP-2, MMP-3; combinations thereof.

In a preferred embodiment, the extracellular matrix component is added by overlaying the population of dedifferentiated cells.

In a preferred embodiment, the cells are cultured for a period of at least 1, 2, 3, 5, 7, 10, 12, 14, 16, 18, 21, 25, 28, 30, 35, 40, 42, 48, 50 or more days.

In a preferred embodiment, at least a portion of the cultured cells form cultivated islet buds (CIBs), preferably cultivated human islet buds (CHIBs). Preferably, at least 1%, 2%, 5%, 10%, 15%, 20%, 25%, 30%, 35%, 40%, 45%, 50% or more of the cultured cells form CIBs. The term "CIBs" and "cysts" are used interchangeably herein. In a preferred embodiment, the CIBs include: islet cells, e.g., α-cells, β-cells, and/or δ-cells; hormone positive islet cells, e.g., glucagon, insulin, somatostatin and/or pancreatic peptide positive cells; duct cells; exocrine cells; combinations thereof. In a preferred embodiment, the CIBs have: increased levels of insulin expression, e.g., as compared to the dedifferentiated pancreatic cells; increased levels of glucagon expression, e.g., as compared to the dedifferentiated pancreatic cells. In a preferred embodiment, the pancreatic cells obtained have the ability to secrete insulin, e.g., the ability to secrete insulin in response to glucose.

In another aspect, the invention features a method of obtaining pancreatic islet cells. The method includes obtaining a population of adult or differentiated pancreatic cells; allowing the population of pancreatic cells to proliferate in the presence of an agent which promotes expansion, e.g., a growth factor, to obtain a dedifferentiated population of pancreatic cells; and adding an extracellular matrix component to the population of dedifferentiated pancreatic cells, to thereby obtain pancreatic islet cells.

In a preferred embodiment, the population of adult or differentiated pancreatic cells can be: a population substantially free of islet cells, e.g., a population from which the islet cells have been removed or have been substantially removed. In a preferred embodiment, the pancreatic cells are human pancreatic cells. In a preferred embodiment, the population of cells includes: duct cells; exocrine cells; duct and exocrine cells; less than about 60%, 50%, 40%, 30%, 20%, 10%, 5%, 1% islet cells. In a preferred embodiment, the population of cells is obtained from cells remaining after islet isolation.

In a preferred embodiment, the population of cells is selected based on the ability to attach to a container, e.g., a culture flask, e.g., a non-sticky culture flask. These cells are also referred to herein as "adherent cells". In another preferred embodiment, the cells that do not attach to the container are removed from the container and cultured in another container until the cells attach. Preferably, the cells that do not attach to the container are removed when at least 1%, 2%, 3%, 5%, 10%, 15%, 20% or more of the surface of the container has cells attached to it. Once the cells attach, they can be used in the methods of the invention. In a preferred embodiment, the adherent cells express low levels or no insulin, e.g., the cells express less than about 600 ng, 500 ng, 400 ng, 300 ng, 200 ng, 150 ng, 100 ng, 50 ng of insulin. In a preferred embodiment, the adherent cells have: less than about 50%, 45%, 40%, 35%, 30%, 25%, 20%, 15%, 10%, 5%, 3%, 2%, 1% the insulin content of an original sample of cells obtained from a pancreas or pancreases; less than about 50%, 45%, 40%, 35%, 30%, 25%, 20%, 15%, 10%, 5%, 3%, 2%, 1% the DNA content of an original sample of cells obtained from a pancreas or pancreases.

In a preferred embodiment, the method includes providing an agent which promotes proliferation of adult or differentiated pancreatic cells. In a preferred embodiment, the agent which promotes expansion is: a polypeptide or fragment or analog thereof which binds TGF-β, e.g., a soluble TGF-β receptor; an antibody which binds TGF-β; an nucleic acid which binds to TGF-β and inhibits TGF-β expression, e.g., a TGF-β antisense molecule; at least one growth factor; combinations thereof. Preferably, the agent is a growth factor or a combination of growth factors. The growth factor can be one or more of: keratinocyte growth factor (KGF); epidermal growth factor (EGF); transforming growth factors-α (TGF-α); hepatocyte growth factor (HGF). Preferably, the growth factor is KGF.

In a preferred embodiment, the cells are allowed to proliferate by placing the cells on a substrate, e.g., a container, e.g., a plastic container, with medium containing an agent which promotes proliferation of adult or differentiated pancreatic cells, e.g., a growth factor, e.g., KGF, EGF, TGF-α, and/or HGF. In a preferred embodiment, the growth factor is a growth factor which promotes the proliferation of pancreatic duct cells, e.g., rapid proliferation of pancreatic duct cells.

In a preferred embodiment, the container is: a plastic container, e.g., a plastic flask, e.g., a non-sticky plastic flask; a plastic container wherein an extracellular matrix protein has been laid down in the container, e.g., plastic container, e.g., plastic flask. In a preferred embodiment, the extracellular matrix protein is laid down by a cell, e.g., the extracellular matrix is laid down by a cancer derived cell line, e.g., a bladder carcinoma cell line, e.g., an A431 cell line. In another preferred embodiment, the extracellular matrix protein is: added to the container; is a laminin, e.g., laminin 5; is a collagen, e.g., collagen I and/or collagen IV.

In a preferred embodiment, the cells are placed on a substrate in a glucose-containing media, e.g., the glucoseontaining media comprises about 4 mM, 6 mM, 8 mM, 10 mM glucose. The media can be serum free. In a preferred embodiment, nicotinamide is added to the media; insulin/transferrin/selenium (ITS) is added to the media; bovine serum albumin (BSA) is added to the media; combinations of nicotinamide, ITS and/or BSA is added to the media.

In a preferred embodiment, the population of cells is: cultured until confluent; cultured until semi-confluent; cultured until the cells form a monolayer. In a preferred embodiment, the population of cells is cultured until at least about 40%, 50%, 60%, 70%, 75%, 80%, 85%, 90%, 95% confluency.

In a preferred embodiment, the population of cells is cultured for at least 1, 2, 3, 5, 10, 14, 18, 20, 25, 30 or more days.

In a preferred embodiment, the dedifferentiated pancreatic cells express a marker indicative of expansion. The marker can be one or more of: cytokeratin; IPF-1; Pref-1; lack of insulin.

In a preferred embodiment, the population of dedifferentiated cells: is a monolayer of cells; has been cultured until semi-confluent; has been cultured until confluent.

In a preferred embodiment, the extracellular matrix component is one or more of: laminin, e.g., laminin 1; collagen, e.g., collagen IV; entactin; heparin sulfate proteoglycan; nidogen. In a preferred embodiment, the extracellular matrix component is a basement membrane derived substance, e.g., a basement membrane laid down by a cell, e.g., a tumor cell, e.g., an Engelbreth-Holm-Swarm (EHS) tumor cell. Preferably, the extracellular matrix component is Matrigel™. In a preferred embodiment, the extracellular component further includes: one or more growth factor(s); one or more matrix metalloproteinase(s) (MMP), e.g., MMP-2, MMP-3; combinations thereof.

In a preferred embodiment, the extracellular matrix component is added by overlaying the population of dedifferentiated cells.

In a preferred embodiment, the cells are cultured for a period of at least 1, 2, 3, 5, 7, 10, 12, 14, 16, 18, 21, 25, 28, 30, 35, 40, 42, 48, 50 or more days.

In a preferred embodiment, at least a portion of the cultured cells form cultivated islet buds (CIBs), preferably cultivated human islet buds (CHIBs). Preferably, at least 1%, 2%, 5%, 10%, 15%, 20%, 25%, 30%, 35%, 40%, 45%, 50% or more of the cultured cells form CIBs. The term "CIBs", "spheres" and "cysts" are used interchangeably herein. In a preferred embodiment, the CIBs include: islet cells, e.g., α-cells, β-cells, and/or δ-cells; hormone positive islet cells, e.g., glucagon, insulin, somatostatin and/or pancreatic peptide positive cells; duct cells; exocrine cells; combinations thereof. In a preferred embodiment, the CIBs have: increased levels of insulin expression, e.g., as compared to the dedifferentiated pancreatic cells; increased levels of glucagon expression, e.g., as compared to the dedifferentiated pancreatic cells. In a preferred embodiment, the pancreatic cells obtained have the ability to secrete insulin, e.g., the ability to secrete insulin in response to glucose.

In another aspect, the invention features a method of inducing dedifferentiation in adult or differentiated pancreatic cells. The method includes: providing a population of adult or differentiated pancreatic cells which include, e.g., duct and/or exocrine cells by selecting cells based on the ability to attach to a substrate, e.g., a container; culturing the cells in a rich medium, e.g., rich DMEM/F12 serum free medium (and optionally a carbon source, e.g., glucose (e.g., 8 mM), to which can be added: an agent which promotes expansion, e.g., a growth factor, and nicotinamide; and culturing till near confluence or substantial epithelial plaques, thereby providing dedifferentiated cells.

In a preferred embodiment, the population of adult or differentiated pancreatic cells can be: a population substantially free of islet cells, e.g., a population from which the islet cells have been removed or have been substantially removed. In a preferred embodiment, the pancreatic cells are human pancreatic cells. In a preferred embodiment, the population of cells includes: duct cells; exocrine cells; duct and exocrine cells; less than about 60%, 50%, 40%, 30%, 20%, 10%, 5%, 1% islet cells. In a preferred embodiment, the population of cells is obtained from cells remaining after islet isolation.

In another preferred embodiment, the cells that do not attach to the container are removed from the container and cultured until the cells attach to the flask. Preferably, the cells that do not attach to the container are removed when at least 1%, 2%, 3%, 5%, 10%, 15%, 20% or more of the surface of the container has cells attached to it. Once the cells attach, they can be used in the methods of the invention. In a preferred embodiment, the adherent cells express low levels or no insulin, e.g., the cells express less than about 600 ng, 500 ng, 400 ng, 300 ng, 200 ng, 150 ng, 100 ng, 50 ng of insulin. In a preferred embodiment, the adherent cells have: less than about 50%, 45%, 40%, 35%, 30%, 25%, 20%, 15%, 10%, 5%, 3%, 2%, 1% the insulin content of an original sample of cells obtained from a pancreas or pancreases; less than about 50%, 45%, 40%, 35%, 30%, 25%, 20%, 15%, 10%, 5%, 3%, 2%, 1% the DNA content of an original sample of cells obtained from a pancreas or pancreases.

In a preferred embodiment, the agent which promotes expansion is: a polypeptide or fragment or analog thereof which binds TGF-β, e.g., a soluble TGF-β receptor; an antibody which binds TGF-β; an nucleic acid which binds to TGF-β and inhibits TGF-β expression, e.g., a TGF-β antisense molecule; at least one growth factor; combinations thereof.

In a preferred embodiment, the agent which promotes expansion is a growth factor or a combination of growth factors. The growth factor can be one or more of: keratinocyte growth factor (KGF); epidermal growth factor (EGF); transforming growth factor-α (TGF-α); hepatocyte growth factor (HGF). Preferably, the growth factor is KGF.

In a preferred embodiment, the growth factor is a growth factor which promotes the proliferation of pancreatic duct cells, e.g., rapid proliferation of pancreatic duct cells.

In a preferred embodiment, the container is: a plastic container, e.g., a plastic flask, e.g., a non-sticky plastic flask; a plastic container wherein an extracellular matrix protein has been laid down in the container, e.g., plastic container, e.g., plastic flask. In a preferred embodiment, the extracellular matrix protein is laid down by a cell, e.g., the extracellular matrix is laid down by a cancer derived cell line, e.g., a bladder carcinoma cell line, e.g., an A431 cell line. In another preferred embodiment, the extracellular matrix protein is: added to the container; is a laminin, e.g., laminin 5; is a collagen, e.g., collagen I and/or collagen IV.

In a preferred embodiment, the media further includes one or more of: insulin/transferrin/selenium (ITS); bovine serum albumin (BSA).

In a preferred embodiment, the cells are cultured in a rich medium with serum, e.g., rich DMEM/F12 with serum (and optionally a carbon source, e.g., glucose (e.g., 8 mM), prior to culturing the cells in a serum free rich medium.

In a preferred embodiment, the population of cells is cultured until at least about 40%, 50%, 60%, 70%, 75%, 80%, 85%, 90%, 95% confluency.

In a preferred embodiment, the population of cells is cultured for at least 1, 2, 3, 5, 10, 14, 18, 20, 25, 30 or more days.

In a preferred embodiment, the dedifferentiated pancreatic cells express a marker indicative of expansion. The marker can be one or more of: cytokeratin; IPF-1; Pref-1; lack of insulin.

In another aspect, the invention features a method of providing islet cells, e.g., alpha cells, beta cells and/or delta cells. The method includes providing a population of adult or differentiated pancreatic cells which include, e.g., duct and/or exocrine cells selected based upon the ability to attach to a substrate, e.g., a container, culturing the cells in the presence of a rich medium, e.g., rich DMEM/F12 serum free medium (and optionally a carbon source, e.g., glucose (e.g., 8 mM), to which is added: an agent which promotes expansion, e.g., a growth factor, and nicotinamide; culturing till near confluence or substantial epithelial plaques, to thereby provide dedifferentiated cells; and contacting the layer of cells with extracellular matrix, or one or more components thereof, thereby providing newly differentiated islet cells.

In a preferred embodiment, the population of adult or differentiated pancreatic cells can be: a population substantially free of islet cells, e.g., a population from which the islet cells have been removed or have been substantially removed. In a preferred embodiment, the pancreatic cells are human pancreatic cells. In a preferred embodiment, the population of cells includes: duct cells; exocrine cells; duct and exocrine cells; less than about 60%, 50%, 40%, 30%, 20%, 10%, 5%, 1% islet cells. In a preferred embodiment, the population of cells is obtained from cells remaining after islet isolation.

In another preferred embodiment, the cells that do not attach to the container are removed from the container and cultured in another container until the cells attach. Preferably, the cells that do not attach to the container are removed when at least 1%, 2%, 3%, 5%, 10%, 15%, 20% or more of the surface of the container has cells attached to it. Once the cells attach, they can be used in the methods of the invention. In a preferred embodiment, the adherent cells express low levels or no insulin, e.g., the cells express less than about 600 ng, 500 ng, 400 ng, 300 ng, 200 ng, 150 ng, 100 ng, 50 ng of insulin. In a preferred embodiment, the adherent cells have: less than about 50%, 45%, 40%, 35%, 30%, 25%, 20%, 15%, 10%, 5%, 3%, 2%, 1% the insulin content of an original sample of cells obtained from a pancreas or pancreases; less than about 50%, 45%, 40%, 35%, 30%, 25%, 20%, 15%, 10%, 5%, 3%, 2%, 1% the DNA content of an original sample of cells obtained from a pancreas or pancreases.

In a preferred embodiment, the agent which promotes expansion is: a polypeptide or fragment or analog thereof which binds TGF-β, e.g., a soluble TGF-β receptor; an antibody which binds TGF-β; an nucleic acid which binds to TGF-β and inhibits TGF-β expression, e.g., a TGF-β antisense molecule; at least one growth factor; combinations thereof.

In a preferred embodiment, the agent which promotes expansion is a growth factor or a combination of growth factors. The growth factor can be one or more of: keratinocyte growth factor (KGF); epidermal growth factor (EGF); transforming growth factor-α (TGF-α); hepatocyte growth factor (HGF). Preferably, the growth factor is KGF. In a preferred embodiment, the growth factor is a growth factor which promotes the proliferation of in pancreatic duct cells, e.g., rapid proliferation of pancreatic duct cells.

In a preferred embodiment, the container is: a plastic container, e.g., a plastic flask, e.g., a non-sticky plastic flask; a plastic container wherein an extracellular matrix protein has been laid down in the container, e.g., plastic container, e.g., plastic flask. In a preferred embodiment, the extracellular matrix protein is laid down by a cell, e.g., the extracellular matrix is laid down by a cancer derived cell line, e.g., a bladder carcinoma cell line, e.g., an A431 cell line. In another preferred embodiment, the extracellular matrix protein is: added to the container; is a laminin, e.g., laminin 5; is a collagen, e.g., collagen I and/or collagen IV.

In a preferred embodiment, the media further includes one or more of: insulin/transferrin/seleniurn (ITS); bovine serum albumin (BSA).

In a preferred embodiment, the cells are cultured in a rich medium with serum, e.g., rich DMEM/F12 with serum (and optionally a carbon source, e.g., glucose (e.g., 8 mM), prior to culturing the cells in a serum free rich medium.

In a preferred embodiment, the population of cells is cultured until at least about 40%, 50%, 60%, 700%, 75%, 80%, 85%, 90%, 95% confluency.

In a preferred embodiment, the population of cells is cultured for at least 1, 2, 3, 5, 10, 14, 18, 20, 25, 30 or more days.

In a preferred embodiment, the dedifferentiated pancreatic cells express a marker indicative of expansion. The marker can be one or more of: cytokeratin; IPF-1; Pref-1; lack of insulin.

In a preferred embodiment, the layer of cells is contacted with an extracellular matrix component which is one or more of: laminin, e.g., laminin 1; collagen, e.g., collagen IV; entactin; heparin sulfate proteoglycan; nidogen. In a preferred embodiment, the extracellular matrix component is a basement membrane derived substance, e.g., a basement membrane laid down by a cell, e.g., a tumor cell, e.g., an Engelbreth-Holm-Swarm (EHS) tumor cell. Preferably, the extracellular matrix component is Matrigel™. In a preferred embodiment, the extracellular component further includes: one or more growth factor(s); one or more matrix metalloproteinase(s) (MMP), e.g., MMP-2, MMP-3; combinations thereof.

In a preferred embodiment, the extracellular matrix component is added by overlaying the population of dedifferentiated cells.

In a preferred embodiment, the cells are cultured for a period of at least 1, 2, 3, 5, 7, 10, 12, 14, 16, 18, 21, 25, 28, 30, 35, 40, 42, 48, 50 or more days.

In a preferred embodiment, at least a portion of the cultured cells form cultivated islet buds (CIBs), preferably cultivated human islet buds (CHIBs). Preferably, at least 1%, 2%, 5%, 10%, 15%, 20%, 25%, 30%, 35%, 40%, 45%, 50% or more of the cultured cells form CIBs. The term "CIBs", "spheres" and "cysts" are used interchangeably herein. In a preferred embodiment, the CIBs include: islet cells, e.g., α-cells, β-cells, and/or δ-cells; hormone positive islet cells, e.g., glucagon, insulin, somatostatin and/or pancreatic peptide positive cells; duct cells; exocrine cells; combinations thereof In a preferred embodiment, the CEBs have: increased levels of insulin expression, e.g., as compared to the dedifferentiated pancreatic cells; increased levels of glucagon expression, e.g., as compared to the dedifferentiated pancreatic cells. In a preferred embodiment, the pancreatic cells obtained have the ability to secrete insulin, e.g., the ability to secrete insulin in response to glucose.

In another aspect, the invention features a method of treating a subject, e.g., a human subject, having a disorder characterized by insufficient pancreatic islet function. The method includes administering pancreatic islet cells obtained by the methods described herein to a subject having a disorder characterized by insufficient pancreatic islet function, to thereby treat the subject.

In a preferred embodiment, the disorder is diabetes, e.g., insulin-dependent diabetes mellitus (IDDM) or non-insulin dependent diabetes mellitus (NIDDM).

In a preferred embodiment, the pancreatic cells are obtained after pancreatic islet cell isolation from a donor pancreas.

In a preferred embodiment, the pancreatic cells are obtained from the subject having the disorder.

In another aspect, the invention features a population of pancreatic cells made by any of the methods described herein.

In a preferred embodiment, the pancreatic cells are islet cells, e.g., alpha, beta and/or delta cells. Preferably, the pancreatic islets are hormone positive islet cells, e.g., glucagon, insulin, somatostatin, pancreatic peptide positive cells, and combinations thereof. In a preferred embodiment, the pancreatic islets have: increased levels of insulin expression, e.g., as compared to the dedifferentiated pancreatic cells; increased levels of glucagon expression, e.g., as compared to the dedifferentiated pancreatic cells. In a preferred embodiment, the pancreatic cells obtained have the ability to secrete insulin, e.g., the ability to secrete insulin in response to glucose.

In another preferred embodiment, the pancreatic cells are dedifferentiated pancreatic cells. Preferably, the dedifferentiated pancreatic cells express a marker indicative of expansion. The marker can be one or more of: cytokeratin; IPF-1; Pref-1; lack of insulin.

The term "pancreatic cell" as used herein refers to a cell obtained from the pancreas. Preferably, the pancreatic cell is a duct cell or an exocrine cell. A "population of pancreatic cells" refers to two or more cells obtained from the pancreas. The cells can be obtained from the same or different pancreases. Preferably, a population of pancreatic cells is substantially free of islet cells, e.g., the population of pancreatic cells comprises less than 70%, 60%, 50%, 45%, 40%, 35%, 30%, 25%, 20%, 15%, 10%, 5%, 3%, 1% pancreatic islet cells.

The terms "CIBs", "spheres" and "cysts" are used interchangeably herein. These terms refer to three-dimensional structures which arise from dedifferentiated pancreatic cells contacted with an extracellular matrix component. Preferably, the CIBs include one or more of: duct cells; exocrine cells; endocrine cells, e.g., cells which stain positive for insulin, glucagon, somatostatin and/or pancreatic peptide; pancreatic islet cells, α-cells, β-cells, and/or δ-cells.

The terms "IPF-1" and "PDX-1" are used interchangeably herein. Other names for "IPF-1" include "STF-1" and "IDX-1".

The term "subject" includes mammals, particularly humans, susceptible to a disease characterized by insufficient insulin activity. Examples of subjects include primates, e.g., humans and monkeys.

Other features and advantages of the invention will be apparent from the following description and from the claims.

BRIEF DESCRIPTION OF THE DRAWINGS

FIG. 1 depicts the three dimensional structures of ductal cysts with protruding buds of islet cells (CHIBs) which are present after the ducts were overlaid with extracellular matrix components (FIG. 1A). in FIG. 1C it is 100 μm; in FIG. 1D it is 50 μm.

DETAILED DESCRIPTION OF THE INVENTION

Figures 1A, 1B:
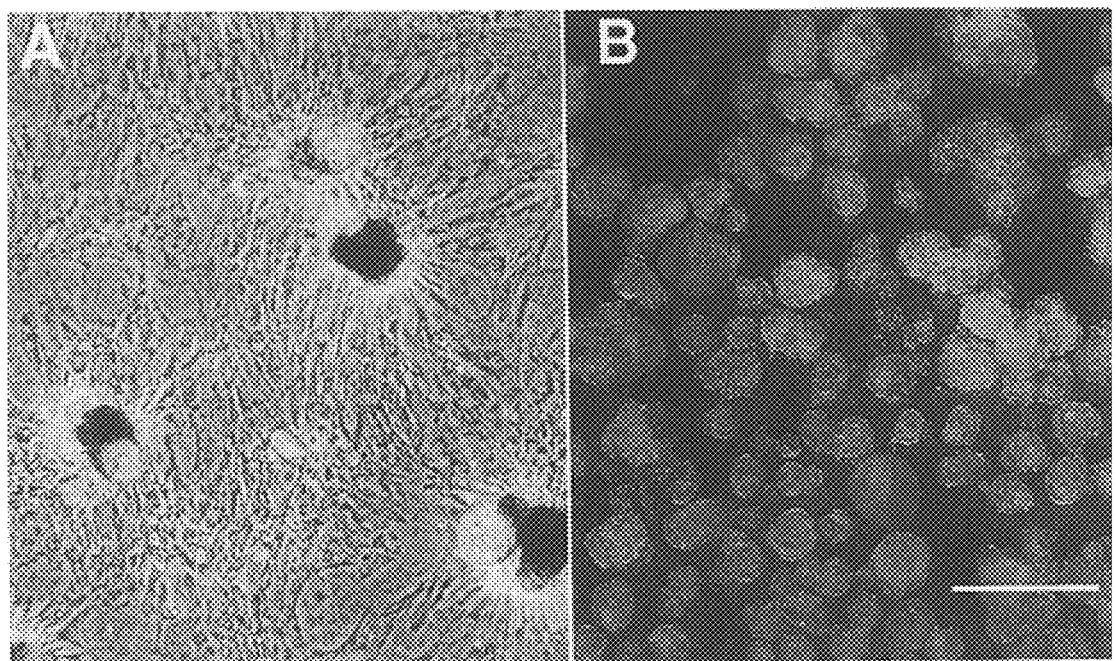
FIGS. 1B and 1C show the variable numbers of dithizone stained β cells in these harvested cysts. Some of these structures have 50–150 μm islet buds.

Protocol for the Production of Pancreatic Islet Cells from Pancreatic Cells

Methods of Obtaining Adult or Differentiated Pancreatic Cells

Pancreatic cells can be obtained from a donor pancreas or pancreases. The pancreatic cells can be provided by a subject to whom the pancreatic islet cell will later be administered. Other sources for providing a pancreatic cell include a cell obtained from a donor other than the subject to whom the pancreatic islet cell will be administered. The donor can be of the same species as the recipient subject (allogeneic) or a different species (xenogeneic). Preferably, the pancreatic cell is obtained after islet purification procedures. However, the pancreatic cell can also be obtained prior to islet purification. After islet isolation procedures, the remaining cells can be cultured in media, e.g., CRML media, preferably with serum. The cells are cultured until cells attach to culture flask, e.g., the cells clump, move to the bottom of the flask and attach to the flask. The flask can be a sticky flask or a non-sticky flask, e.g., a bacteriological flask. Preferably, a non-sticky flask is used, e.g., a flask which maintains islets in suspension. Generally, cells will clump and attach to the flask in about 1–10 days, 1–4 days.

Cells that do not attach to the flask can be removed and placed in a new flask. Preferably, the cells that do not attach to the flask are removed when at least 1%, 2%, 3%, 5%, 10%, 15%, 20% or more of the surface of the flask has cells attached to it. The non-attached cells can then continue to be cultured in media, e.g., CRML media, e.g., CRML media plus serum, until they attach to the flask. This process can continue to be repeated to obtain cells for use in the methods. The cells that do attach are also referred to herein as "adherent cells".

Cells obtained by this procedure are mostly non-islet cells, e.g., duct tissue and exocrine cells. However, the population of cells can comprise pancreatic islet cells, e.g., the population of cells can comprise less than 70%, 60%, 50%, 40%, 30%, 20%, 15%, 10%, 5%, 1% pancreatic islet cells. Examples of pancreatic islet cells include alpha, beta and delta cells. Methods of determining the type of cell in a population of pancreatic cells can be determined using methods known in the art. For example, the cells can be stained with a stain specific for a particular cell type, e.g., an islet specific stain, e.g., dithizone stain. Other methods for determining a particular cell type include double immunofluorescence staining, e.g., using antibodies made in different species which bind to various pancreatic cell specific proteins, e.g., insulin, somatostatin, glucagon, pancreatic polypeptide, and a label conjugated to an antibody which binds to the antibodies of a particular species. In addition, a cell type can be determined by its morphology, e.g., non-islet cells have a clear epithelial morphology.

The cells can be diluted in the container, e.g., flask, such that there is greater epithelial growth than fibroblast growth achieved. For example, the cells can be diluted to achieve a final concentration of 1.5 to 3 million cells in a 75 cm$^2$ flask.

Methods of Promoting Proliferation of Adult or Differentiated Pancreatic Cells

The attached cells can be expanded, e.g., the cells can be expanded for about 1–20 days, 4–16 days, 7–14 days. During the expansion period, the media can be changed, e.g., about every 2–3 days, or it can remain unchanged. The attached cells can then remain in the same container or can be lifted and introduced into a new container. The cells can then be lifted, for example, with a trypsin solution. Cells treated with trypsin solution become rounder and can be shaken off the flask and spun down. The cells can then be diluted in a new container, e.g., flask. Preferably, the cells are diluted such that there is greater epithelial growth than fibroblast growth.

The container is preferably a flask, e.g., a plastic flask. The cells can either be in a flask, as is, or a flask in which an ECM has been laid down. ECM, or components of ECM, can be laid down by a cell. For example, a cell line derived from a tumor such as a bladder carcinoma cell line, e.g., A431 cell line, can be cultured till confluence or semiconfluence in a container, e.g., a plastic container, e.g., a plastic flask. The tumor-derived cells can then be killed and washed off to obtain a container which comprises ECM, or a component or components of ECM. An ECM component can also be added to the container, e.g., collagen. Preferably, an ECM protein associated with tumors such as laminin 5 is added to the container. Synthetic ECM replacements can also be used.

The cells are allowed to proliferate by, for example, placing the cells on a substrate, e.g., a container, with media or by adding the media to the container. Preferably, the media includes glucose. For example, the glucose-containing media can include about 4 mM, 6 mM, 8 mM, 10 mM glucose. A preferred media is DMEM/F12, preferably serum free DMEM/F12. However, the cells can initially be cultured in media with serum added. For example, the cells can be cultured for about 24–48 hours in the presence of serum and then the media is changed to be serum free. At least one or more of the following can be added to the serum free media: an agent which promotes expansion, e.g., a growth factor,; nicotinamide; insulin/transferrin/selenium (ITS); and/or bovine serum albumin (BSA). Agents which promote expansion include KGF, EGF, TGF-α, TGF-β and HGF.

The cells are cultured till near confluence or substantial epithelial plaques. Preferably, the cells are cultured until at least about 40%, 50%, 60%, 70%, 75%, 80%, 85%, 90%, 95% confluency. This procedure promotes rapid proliferation of non-islet tissue, e.g., duct tissue, to dedifferentiate and become pluripotent. Markers indicative of pancreatic expansion can be used to detect dedifferentiated pancreatic cells. Such markers include one or more of: cytokeratin, PDX-1, IDX-1, STF-1, IPF-1 (PDX-1/IDX-1/STF-1), Pref-1 and lack of insulin.

Methods of Obtaining Pancreatic Islets from Dedifferentiated Pancreatic Cells

The dedifferentiated (pluripotent) cells can then be used to obtained islet cells, as well as duct cells and exocrine cells. Differentiation of the pluripotent cells can be achieved by contacting, e.g., overlaying, the monolayer of cells with ECM, or a component or components of EMC. Preferably, the layer of cells is contacted with an extracellular matrix component which is one or more of: laminin, e.g., laminin 1; collagen, e.g., collagen IV; entactin; heparin sulfate proteoglycan; nidogen. The extracellular matrix component can be a basement membrane derived substance, e.g., a basement membrane laid down by a cell, e.g., a tumor cell, e.g., an Engelbreth-Holm-Swarm (EHS) tumor cell. Preferably, the extracellular matrix component is Matrigel™ which is commercially available from Becton-Dickenson. The extracellular component can further include: one or more growth factor(s), one or more matrix metalloproteinase (s) (MMP), e.g., MMP-2, MMP-3, and combinations thereof.

The cells can be cultured in the presence of the extracellular matrix or component or components of the extracellular matrix for a period of at least 1, 2, 3, 5, 7, 10, 12, 14, 16, 18, 21, 25, 28, 30, 35, 40, 42, 48, 50 or more days.

The cells are then allowed to differentiate and spheres of tissue form which include newly differentiated islet cells. These spheres or tissue are also referred to as cultivated islet buds (CIBs). Preferably, at least 1%, 2%, 5%, 10%, 15%, 20%, 25%, 30%, 35%, 40%, 45%, 50% or more of the cultured cells form CIBs. The CIBs can include: islet cells, e.g., α-cells, β-cells, and/or δ-cells; hormone positive islet cells, e.g., glucagon, insulin, somatostatin and/or pancreatic peptide positive cells; duct cells; exocrine cells; combinations thereof. These carious cell types can be determined, for example, by the staining methods described above. Preferably, the CIBs have: increased levels of insulin expression, e.g., as compared to the dedifferentiated pancreatic cells; increased levels of glucagon expression, e.g., as compared to the dedifferentiated pancreatic cells, and/or have the ability to secrete insulin, e.g., the ability to secrete insulin in response to glucose.

Using known islet isolation procedures, about 600,000 islets are about the most that can be isolated from a single pancreas, and usually the yield is not that high. If the remaining non-islet tissue left from the digestion and purification of the pancreas is retrieved and grow as described herein, then the isolated islets may be supplemented with equal numbers of in vitro grown islets. Potential yields of in vitro grown islets by the methods described herein are about 500,000 islets or more.

Pancreatic Duct Cells as Islet Precursor Cells

Pancreatic duct cells are capable of serving as precursor cells and are, thus, facultative stem cells. The term "facultative stem cells" means that at least a portion of the duct cells such as duct epithelium and/or acini are capable of serving as precursor cells. In addition, exocrine cells are capable of serving as precursors. Clonal expansion of these "facultative stem cells" has been achieved in vitro. Successful passaging of pancreatic ducts for 20–30 passages has been accomplished. These cells lose their ductal phenotype but regain duct and islet phenotypes in vivo. Thus, by replication, a mature duct cell can revert to a less differentiated cell that can then redifferentiate into islet, exocrine or mature duct cell. External signals can direct the phenotypic differentiation. Signals involved in proliferation and differentiation of these precursor pancreatic cells can include: cell-cell and cell-matrix interactions and growth factors/cytokines. Examples such factors include: extracellular matrix components such as laminins (e.g., laminin I and/or laminin 5), collagen (e.g., collagen I and/or collagen IV), heparin sulfate proteoglycans, entactin, and nidogen; proteins or peptides which interact with extracellular matrix components such as integrins; growth factors (e.g., TGF-α, TGF-β, KGF, HGF and/or EGF) and their receptors.

Various models can be used to determine which factors are involved in pancreatic cell dedifferentiation and subsequent regeneration. The partial pancreatectomy (Px) model has been used as a well defined system of in vivo growth and development, with a rapid and defined time line. Using this model, it was found, for example, that both HGF and TGF-β have marked changes in expression during the first days after Px. In addition, primary duct cultures can be used to determine the direct effect of these factors in vitro. Using primary cultures, the direct effects of HGF and TGF-β on the proliferation of ductal epithelium was determined. PDX-1/PDX-1 protein expression in these ducts has also suggested that the mature ducts undergo dedifferentiation with proliferation, being facultative stem cells. To further understand the mechanisms involved in pancreatic differentiation/dedifferentiation, changes of matrix and cell-matrix adhesion molecules have been analyzed in vivo and then use in an in vitro system to dissect phenotypic changes induced by rapid replication from those induced by the cytokines expressed after Px.

In an effort to further characterize the precursor cells, a partial pancreatectomy was also performed in streptozocin (STZ) treated rats that had been transplanted with enough islets to maintain normoglycemia This model was used to determine whether the ductal precursor cells expressed enough β cell specific characteristics to be damaged by the STZ. Since ducts proliferated and differentiated into both islets and exocrine tissue, it can be concluded that the STZ did not affect the precursor cells. Furthermore, the reduction of β cell mass of greater than 70% by pretreatment with STZ had no effect on regeneration of either endocrine or exocrine tissue in the remnant after Px. There was no correlation between the fed plasma glucose levels and the mass of regenerating tissue.

External Factors Involved in Pancreatic Differentiation/Dedifferentiation

The external signals most epithelial cells rely on for initiation and maintenance of their differentiated phenotype are cell-cell and cell matrix interactions and growth factors/cytokines. Various factors can be tested using multiplex RT-PCR and/or immunolocalization on pancreas after Px. For example, using these methods, it was found that HGF and TGFβ expression change during pancreatic regeneration. Changes induced by these factors may regulate the expression of matrix binding proteins and matrix proteins which results in ductal expansion and redifferentiation. The in vivo system allows for characterization of the duct precursor cells in the adult pancreas and how their differentiation is regulated, while a complementary in vitro expansion of duct cells allows manipulation and molecular analysis of the mechanisms involved in the differentiation process.

Factors were studied to identify those factors involved in the regenerating pancreas for proliferative, morphogenic and differentiating effects on cultured ductal epithelium. First, the primary cultures were characterized. Collagen I, collagen IV, laminin, and Matrigel coated culture dishes have all been found to support the growth of primary ductal epithelium with some cells differentiating to become insulin positive with immunostaining. The morphology of the cells can differ somewhat on the different matrices. The media was also changed to a "richer" one (DMEM/Ham's F12) with added nictotinamide and found increased differentiation. Immunostaining of BrdU (10 uM) incorporated into newly synthesized DNA during the last 4 hours of a 48 hour culture period on collagen I shows massive incorporation of BrdU in the ductal epithelium, even with BrdU labeled mitotic figures and daughter cells. It was found that 32.5+ 4.4% of the cells are in replication during a 4 hour time when Px+3 day ducts are used. Surprisingly, ducts from sham operated animals show a similar replication rate. These results suggest that in culture the ductal cells have been released from an inhibitory state.

Secondly, the primary duct cultures have proved valuable for testing the proliferative and differentiative effects of TGF-β and HGF. Since TGF-β is a factor often inhibiting epithelial growth and its immunolocalization pattern supported such a role in pancreas (see below), it appears that TGF-β may act as a brake on ductal proliferation. When this factor (10 ng/ml, human recombinant TGF-β, R&D Systems) was added for the last 24 hours of culture on collagen I gels, a profound cessation of the replication, down 10 fold to 3.3 f 0.6%, was found. A similar finding was seen with Matrigel-coated dishes, but the replication levels were less. These data support the conclusion that TGF-β could have a major role in regulating the ductal expansion that is the first step of regrowth of the pancreas. The addition of HGF (10 or 50 ng/ml) for the last 48 hours of primary duct epithelium on Matrigel increased the BrdU incorporation of cultured primary duct epithelium 2–3 fold (10 ng/ml HGF 11.8 f 2.3%; 50 ng/ml, 14.8+2.1%; untreated control 4.9+ 0.9%). These data, compared to those above on collagen I, that the matrix influenced the basal replication rate show that primary duct cells proliferate at a greater rate on collagen I than on Matrigel. The addition of HGF to the culture medium did not produce any apparent changes in the number of hormone positive cells, leading to conclusion that HGF has a proliferative and not differentiative role in this system.

Thirdly, innumerable variations on culturing the primary duct cells in three dimension gels have been tested. In each case with additional culture time, there is a digestion of the matrix by the explanted tissue. It was found by immunofluorescent staining for cytokeratin 20 (duct epithelium) and vimentin (fibroblasts) that subepithelial fibroblasts remaining on the explant started to proliferate by 96 hours. It appears that they were induced to produce matrix metalloproteases that digested the overlying matrix.

Other candidate factors were also assessed for involvement. Not only were the soluble factors defined in the regenerating pancreas studied, but also a number of other proteins including some for which null mice have been recently generated.

In addition, mechanisms which lead to proliferation and dedifferentiation of the duct cells in the common pancreatic duct after partial pancreatectomy can be observed. Epithelial cells rely on cell-cell and cell matrix interactions for initiation and maintenance of their differentiated phenotype. Thus, growth, organogenesis and regeneration all involve the regulation of extracellular matrix and the cell's matrix binding proteins (particularly integrins but including non integrin laminin binding proteins) often by soluble factors, such as HGF and TGFβ. For example, the changes in both of these factors in the pancreatic regeneration after partial pancreatectomy have been mapped and appears that changes induced by these factors regulate the expression of matrix binding proteins and matrix proteins and that these changes result in ductal expansion and redifferentiation.

Exendin-4

Exendin-4, which is a homolog of GLP-1, has been found to increase β cell replication and differentiation from duct cells. Thus, exendin-4 can be used to promote differentiation of dedifferentiated cells into pancreatic islet cells, e.g., β-cells.

Using an immortalized cell line derived from mice, data has been obtained which shows that exendin-4 alone or with betacellulin, can cause transcription of the insulin promoter. In parallel, exendin-4 was also used in vivo after Px. For the first 10 days after Px, exendin-4 (1 nmol/kg) was given intraperitoneally. Plasma glucose levels and body weights were followed weekly until sacrifice at 4 weeks after Px. The Px+exendin rats had significantly lower plasma glucose levels from 2 weeks onwards even though the treatment was stopped at 10 days. In pancreatic sections of these rats, the β cell mass appears increased, both as islets and small clusters of hormone positive cells budding from the ducts; quantification of the beta cell mass is in progress. The in vivo and in vitro data suggest that exendin-4 stimulates both differentiation of ducts and beta cell replication.

Since exendin-4 has been found to increase both β cell replication and differentiation from ducts (neogenesis), it can be used to modulate increases of β cell mass, e.g., in vivo.

Growth Factors & Extracellular Matrix Components

Regulation of growth, generally, arises from a sequential expression of different growth factors and from differential responses of multiple receptors of the same family. Many interactions are dependent on cell contact with other cells or with extracellular matrix. Several growth factors, extracellular matrix components and their ligands have been found to play a role in differentiation/dedifferentiation of pancreatic cells. Thus, different growth factors and ECM components may be useful in producing pancreatic islet, duct and exocrine cells from dedifferentiated pancreatic cells and/or for expanding dedifferentiated pancreatic cells prior to differentiation.

Integrin, Matrix Metalloproteases and their Interactions with ECM

Cell-matrix interactions involve integrin and non-integrin receptors that have specificity of binding to ECM components (for example, α6β1 and α7β1 for laminin 1; α4β1 and α5β1 for fibronectin; α6β1 for laminin 5 (epiligrin) and collagen, fibronectin and laminin 1; αvβ1 for fibronectin and vitronectin) resulting in different responses within a cell. In the pancreas, β1 integrin subunits are highly expressed on pancreatic epithelial cells, but there are discrepancies as to which α subunits are present. Levine et al. (1994) *Cell Transplant.* 3:307–313. In one report of normal human pancreas and chronic pancreatitis, α2,3,6 v, 1, m, and x subunits were found whereas α2,3 and 6 are more intense with adenocarcinoma. Shimoyama et al. (1995) *Int. J. Pancreatol.* 18:227–234. In another, α2 and 6 were seen in all parenchyma, α3 and v only in ducts (which also have β4 subunits) and none were seen in islets. Hall et al. (1991) *J. Pathol.* 165:33–41. However, in recent studies, rat islets were reported to have considerably more α3 integrin subunit than acinar and at least 50% of the islet α subunits associated with β1 were α3. Kantengwa et al. (1997) *Exp. Cell Res.* 237:394–402. It has been suggested that α6β1 integrins were present on beta cells and increased with secretagogues (high glucose, glucagon or IBMX). Bosco et al. (1998) *Diabetologia* 41:A66. Further, when β cells are spread on a laminin 5 rich matrix (804G), they had both a higher insulin secretion in response to glucose and more α6β1 integrin. It has also been shown that fetal pancreatic tissue and adult islets have a greater response to hepatocyte growth factor (HGF) if the tissue is grown on species-specific matrix with high laminin 5 content. Hayek et al. (1995) *Diabetes* 44:1458–1460; Beattie et al. (1997) *J. Clin. Endocrinol. Metabol.* 82:1852–1856. The rat pancreatic ductal carcinoma derived cell line AR42J has been shown to have more affinity to laminin than type IV collagen or fibronectin, but there is differential expression and binding to at least two laminin receptors (only one of which is an integrin) depending on its differentiative state. Stallmach et al. (1992) *Gastroenterol.* 102:237–247. AR42J cells in undifferentiated state attached to laminin via 67 kD laminin receptors while after dexamethasone treatment, a treatment that others have shown to induce acinar differentiation, they adhered via α6β1 integrins. Stallmach et al. (1992) *Gastroenterol.* 102:237–247. In sectioned islets, α3β1 integrin was expressed on all plasma membrane faces of beta cells even where there was no laminin 1 or 5 (Kantengwa et al. (1997) *Exp. Cell Res.* 237:394–402), which is consistent with α3β1 playing a role in cell-cell adhesion as well as cell matrix. Symington et al. (1995) *J. Cell Sci.* 108:831–838; Carter et al. (1991) *Cell* 65:599–610. However, normal islet and pancreatic morphology was found in transgenic mice with a mutant α3 integrin that lacks function. These mice, with severe malformations of the lung and kidney, die at birth so functional abnormalities in the islets could still exist. Kreidberg et al. (1996) *Development* 122:3537–3547. This finding suggest that integrin or matrix binding proteins other than α3 are present in the pancreas during morphogenesis. Another aspect to consider is that extracellular matrix is usually remodeled during development, regeneration, or with neoplasia. Kim et al. (1997) Hepatology 26:896–904. One of the key mechanisms for such remodeling is the induction of matrix metalloproteases (MMPs) that are not constitutively expressed. Matrisian et al. (1990) *Trends Genet.* 6:121–125. Soluble growth factors such as TGFβ, EGF, HGF regulate the expression of integrins, matrix components and MMP, while MMPs can regulate the conversion from latent TGFβ and proHGF to active molecules. Matrisian et al. (1990) *Trends Genet.* 6:121–125; Mizushima et al. (1996) *J. Biochem.* 120:1196–1202; Kim et al. (1997) *Proc. Soc. Exp. Biol. Med.* 214:123–131; Lochter et al. (1997) *J. Cell. Biol.* 139:1861–1872; Kumar et al. (1995) *Exp. Cell Res.* 221:385–394. There are several MMPs with different specificities but all can be blocked by zinc chelation, all are secreted by stromal cells in a latent form that can be converted to an active form by urokinase plasminogen activator (u-PA). Matrisian et al. (1990) *Trends Genet.* 6:121–125. MMP-1 mainly degrades collagen I, II, and III; MMP-3 (stromelysin) degrades proteoglycans, laminin, collagens III, IV, and V, and gelatins; MMP-2 (72 kD type TV collagenase, gelatinase A) mainly degrades collagens IV, V, and VII, fibronectin and gelatins. Matrisian et al. (1990) *Trends Genet.* 6:121–125. In addition, MMP2 specifically cleaves laminin 5 and exposes a cryptic site that triggers cell mobility. Giannelli et al. (1997) *Science* 277:225–228. MMP-2, and not MMP-1, MMP3 was seen in chronic pancreatitis (Gress et al. (1994) *Gastroenterol.* 32:221–225), and so is the most likely MMP in the remodeling seen here. MMP-3 is another likely candidate since it triggers phenotypic changes in mammary duct epithelium by altering cell-cell interactions while inducing MMP-2 and keratinocyte growth factor (KGF). Lochter et al. (1997) *J. Cell Biol.* 139:1861–1872. After injury or surgery urokinase-plasminogen activator (u-PA) protein and its receptor can rapidly increase in the epithelium and initiate a rapid degradation of matrix components and activate proHGF and latent TGFβ. Kim et al. (1997) *Hepatology* 26:896–904. Up-regulation of urokinase plasminogen activator, and its receptor, gene and protein expression was also found in a pancreatic tumor cell line (IMIM-PC2) following treatment with HGF. Paciucci et al. (1998) *Am. J. Pathology* 153:201–212. Further complexities include that TGFβ has been shown to modulate HGF secretion from fibroblasts. Seslar et al. (1995) *Endocrinology* 136:1945–1953. In fact, the evidence suggests a complex regulatory network in which: 1) HGF causes a dose dependent increase in expression of u-PA and its receptor; which 2) further activates pro HGF; 3) u-PA activates plasminogen to plasmin; which 4) activates TGFP; which 5) inhibits HGF expression, induces its own expression, and down regulates u-PA; which 6) leads to loss of TGFP activity; which 7) removes the constraints on the HGF expression, and the cycle repeats. Seslar et al. (1995) *Endocrinology* 136:1945–1953.

Integrin patterns and binding are likely to provide differentiative responses to pancreatic cells. Thus, integrins and their ligands or binding portions thereof maybe useful in dedifferentiation/differentiation of pancreatic cells.

To determine integrin patterns in pancreatic cell differentiation, changes of matrix and cell-matrix adhesion molecules in pancreatic regeneration model can be correlated temporally and spatially to previous data on the expression of TGFβ and HGF, and then direct evidence of the regulation of the adhesion molecules can be tested with cultured duct cells. Primary cultures of rat common pancreatic ducts show that the amount of α6β1 expressed on recently proliferating duct cells depended on the matrix the cells were grown on. On Matrigel, all cells had intense plasma membrane staining. On collagen I, most cells had strong but less intense staining. On A-431 (a human epidermoid cell line that lays down a laminin 5-rich matrix), some cells had little to no staining while others had strong to intense staining. Since it was found that there are in vivo changes after Px in both HGF and TGFβ expression around the ducts and that the ECM show marked structural changes by 24 hours, it appears that the expression of α3β1 and α6β1 integrins are modulated during the ductal expansion and redifferentiation in the focal areas. Thus, it is likely there are changes in the ECM around the ducts during the expansion/redifferentiation. To test this, pancreatic remnants at 4, 12, 18, and 24 hours and 2, 3, 7 days after Px and the equivalent tissue from unoperated Sprague-Dawley rats can be excised, fresh frozen in chilled isopentane and stored at −80° C. until sectioned. Before staining, sections are fixed in formalin or acetone. These cryostat sections with the common pancreatic duct are then immunofluorescently stained singly, or doubly, for integrin subunits and ECM components. The following antibodies, used for immunochemical staining in published reports, can be used: mouse anti a3p1 integrin (m-kd102, Chemicon), mouse anti α6β1 (MCA2034, Serotec), rabbit anti α3 integrin (AB1920, Chemicon), mouse anti epiligrin/laminin 5 (MAB 1949, Chemicon), rabbit anti rat laminin 1 (A106, GIBCO/BRL). An antibodies to the 67 kD non-integrin laminin receptor; can be obtained as described in the art. (Privitera et al. (1998) *J. Biol. Chem.* 273:6319–6326). The immunostained sections can be studied on the Zeiss LSM microscope. Special attention is to be given to changes in the epithelium of the common pancreatic ducts and of the small ductules of the regions of regeneration. The early time points are relevant for the initial expansion whereas the later time points are for the differentiation of the expanded ductules to exocrine, islet and mature ducts. In vitro evidence has shown that the integrin α6β1 staining intensity varies with underlying matrix, so it is expected that there will be changes in the laminin binding proteins in the duct epithelium after Px. These experiments should define changes in integrins and matrix. It can then be tested in vitro whether these changes are induced directly by TGFβ or HGF or indirectly by changes in the matrix.

In addition, tissue sections can be used to identify marked changes in the laminin composition of the ECM. For epithelial cells, the laminins are important for differentiation (Streuli et al. (1991) *J. Cell. Biol.* 115:1383–1395). While laminins are usually the product of the connective tissue/stromal cells (Simon-Assmann et al. (1990) *Digestion* 46:12–21), human pancreatic carcinoma cell lines can synthesize and deposit laminin 5, which is the preferred strata for movement for these carcinoma cells. Tani et al. (1997) *Am. J. Pathol.* 151:1289–1302. It is likely that rapidly replicating duct cells also synthesize and deposit laminins to allow for the increasing ductal tree. Thus, laminins may be useful for expanding adult or differentiated pancreatic cells. In addition, laminins may play a role in differentiation of dedifferentiated pancreatic cells.

It has also been observed that at 12 and 24 hours after Px marked ultrastructural changes in the stroma adjacent to the common pancreatic duct and digestion of matrix in primary duct cultures. Therefore, changes in the laminin composition in the ECM after Px is expected. One of the key mechanisms for such remodeling is the induction of matrix metalloproteases (MMPs). Matrisian (1990) *Trends Genet.* 6:121–129. Soluble growth factors such as TGFP, EGF, HGF regulate the expression of integrins, matrix components and MMPs, while MMPs can regulate the conversion from latent TGF and proHGF to active molecules. Lochtner et al. (1997) *J. Biol. Chem.* 139:1861–1872; Sakurai et al. (1997) *Amer. J. Physiol.* 273:F463–472; Matrisian (1990) *Trends Genet.* 6:121–129; Mizushima et al. (1996) *J. Biol. Chem.* 120:1196–1202. Then in feedback loops, increases in activated TGFβ and HGF would influence both the matrix and the epithelial cells ability to respond to the matrix. Based on this background, it appears that MMP-2 and/or MP3 are induced shortly after Px and possibly again in the focal areas when the ductules are branching.

To test the induction of these genes, common pancreatic ducts can be isolated from rats at 4, 8, 12, 18 and 24 hours and 2, 3, and 7 days after Px for RNA extraction. Because MMPs are expressed in the stromal cells and not the epithelium, the ducts of stroma are not cleaned as usual but rather just adherent islets and acini are removed. The RNA can then be analyzed using multiplex RT-PCR with primers for both MMPs and an internal control. Cyclophilin, α-tubulin or 36B4 can be used as internal controls. Since MMPs are not constitutively expressed (Matrisian (1990) *Trends Genet.* 6:121–129), the induction of either mRNA suggests that this MMP is active in the matrix remodeling. As is seen in other systems, MMPs may be sequentially expressed, thus, if more than one MBP is expressed at the 24 hr time point, RNA from intermediate times can be examined to determine which was induced first. Since isolated ducts are being used for the RNA, there should not be interference from the focal regions which are not included in the standard isolated duct preparation. If previous immunostaining of matrix suggested a second matrix remodeling in the focal regions, either immunostaining for the MMPs or in situ hybridization can be used to characterize the MMPs involved.

To understand the regulation of the MMP expression, in vitro studies using cultured subepithelial fibroblasts from rat common pancreatic ducts (see Progress Report) can be performed. These in vitro studies test whether HGF, EGF and/or TGF-β regulate the expression of MMPs in these fibroblasts. Fibroblasts are seeded in 6 well plates with DMEM-F12 10% FBS and allowed to become near confluent. The media is then changed to serum free medium, and the cells are cultured 24 hours. Then HGF (10–40 ng/ml, R&D), EGF (40 ng/ml, Collaborative Research) and TGFβ (long/ml, R&D) are added for 24 hrs, after which RNA can be extracted. As controls, wells having no added cytokines can be used. Additionally, neutralizing antibodies for HGF, TGFβ (both R&D) or EGF (GIBCO/BRL) can be added to remove any endogenous cytokine that may confound interpretation. The expression of MMP mRNA can again be assessed by multiplex RT-PCR and compared to that of the untreated cells.

These experiments should greatly advance our understanding of the mechanism of matrix degradation that occurs in vivo after Px. In addition knowing what factors are involved in matrix degradation, and having then the potential to inhibit them, should overcome the difficulties of 3 dimensional cultures that may be useful for in vitro differentiation studies.

TGFα and TGFβ:

TGFα, EGF and/or agents which interfere with TGF-β activity, e.g., TGF-β binding, can be used to promote proliferation of adult or differentiated pancreatic cells.

The proliferation of ductal epithelium by TGFα/EGF has been shown by its overexpression in the pancreas in transgenic mice (Jhappan et al. (1990) *Cell* 61:1137–1146) and by in vitro studies (Verme et al. (1990) *Am. J. Phsyiol.* 258:G833–G840). It has been found using the TGFα overexpressing transgenic mice suggested that TGFα stimulates proliferation of the precursor cells within the adult ducts. Wang et al. (1993) *J. Clin. Invest.* 92:1349–1356. In the Px model, no changes in TGFα mRNA were seen by Northern gel analysis nor in TGFα immunostaining across the time line. It was found that TGFα null mice showed normal pancreatic morphology, suggesting a redundancy of action by various EGF family members. Other studies can be performed to determine which members of this family are important contributors.

In many tissues, TGFβ is a growth inhibitor and is antagonistic to the effects of TGFα and EGF. Studies were performed to determine if TGF-β could have an inhibitory role in the proliferation of the ducts, thus being one of the regulatory elements in the system. If this were true, then TGFP must be expressed close to the duct epithelium and must change in its expression. Immunostaining with an antibody to the mature form of TGF-β (CC 1–30) showed that TGF-β was localized extracellularly around the larger ducts at the interface of the epithelium and stroma in normal pancreas (sham operated and unoperated) or pancreas 12 hours after Px.

However its immunostaining was markedly diminished at times of ductal proliferation (24 hrs–36 hrs after Px) but was stronger again in the newly quiescent ducts at 72 hrs. The pattern and timing of the localization suggests that TGF-β acts as an autocrine or paracrine brake on ductal proliferation, in opposition to TGFα/EGF which stimulate ductal growth. However, when a probe for the mature form of TGF-β generated by PCR (a probe that did not discriminate between the isoforms of TGF-β) was used in a S1 nuclease analysis of total pancreatic RNA 1,2,3,7 and 14 days after Px or sham surgery, it was found that there was a marked enhancement at days 1–3 with a diminishing amount at 7 and then 14 days. Discrepancies with the immunolocalization of TGFβ protein in the extracellular compartment can be explained by the fact that TGF-β transcription often precedes its translation by several days. Romeo et al. (1993) *Mol. Endocrinol.* 7:759–766. To determine whether TGF-β acts as a brake on ductal proliferation, primary duct cultures were treated with TGF-β for the last 24 hours of culture. When this factor (10 ng/ml, human recombinant TGF-β, R&D Systems) was added for the last 24 hours of culture, a profound cessation of the replication was found, down 10 fold to 3.3±0.6%, thus supporting the conclusion that TGF-β could have a major role in regulating the ductal expansion that is the first step of regrowth of the pancreas. Based on RT-PCR analysis of RNA from freshly isolated common pancreatic duct and 3 day primary duct cultures and by in situ hybridization, it can be concluded that TGF-β was an autocrine inhibitor of ductal epithelium. The TGF-β found around the major ducts is secreted by the epithelial cells themselves. The role of TGF-β is multifaceted in a number of tissues regulating the expression of integrins, extracellular matrix components and other growth factors/cytokines.

Hepatocyte Growth Factor (HGF):

HGF can be used as an agent to promote expansion of adult or differentiated pancreatic cells.

A study of the expression of hepatocyte growth factor (HGF) and its receptor, c-met, in pancreas regeneration was performed. After Px, HGF mRNA levels in the pancreatic remnant were not significantly increased above those in unoperated animals by semiquantitative RT-PCR. Only at one time point (2 days) was there an increase. Since the pancreatic remnant is composed of a mixture of duct, exocrine and islet cells, the common pancreatic ducts of unoperated, sham-operated and partially pancreatectomized rats were isolated for further RT-PCR studies to detect HGF and c-met mRNA. While there was some minor variation among animals, there was no significant change in HGF mRNA during the week (4 hour–7 days) of active regeneration following the surgery. For c-met mRNA from the isolated ducts, there was no difference at any one time point, but overall a significant decrease after Px. Similarly, HGF protein levels did not increase during after Px as determined by Western blot analysis.

Since the isolated common pancreatic duct consisted of both the columnar epithelium of this duct and a residual amount of closely adherent stroma, it was important to localize each protein by immunostaining. In sham and Px rat pancreas, HGF was immunolocalized both to the cytoplasm of the epithelial cells as well as that of single stromal cells surrounding the common pancreatic duct and was particularly prominent in the evaginations, characteristic of the common pancreatic duct. Staining was largely absent from the exocrine tissue. HGF staining was more intense 1–3 days after Px than after sham Px; by 7 days staining was comparable between Px and sham. Similar staining of duct epithelium and connective tissue cells was also seen in the areas where ductal cells are undergoing expansion to form new pancreatic tissue (focal areas of regeneration). The receptor for HGF, c-met, immunolocalized to the plasma membranes of some duct epithelial cells (both in the larger ducts and in the small ductules of focal regions of regeneration) and of the non-B cells of the islet periphery. This islet staining was mainly observed in the Px animals and little to no staining was seen in pancreatic beta or exocrine cells. This data does not support the role of HGF in the enhanced proliferation of the pre-existing beta cells in this rodent model but rather as both an autocrine and paracrine mitogen for the ductal epithelium.

Gastrin and CCK:

Gastrin has been found to increase differentiation of islet endocrine cells. Thus, gastrin can be used to promote differentiation of dedifferentiated pancreatic cells into pancreatic islets.

Studies with the double transgenic mice which had both overexpression of gastrin and TGFα in the pancreas suggested that gastrin may facilitate the differentiation of the precursor cells to islet endocrine cells possibly by inhibiting the proliferative effect of TGFα. Interactions between EGF and CCK, homologues of TGFα and gastrin respectively, have been shown. Romeo et al. (1993) *Mol. Endocrinol.* 7:759–766; Korc et al. (1984) *PNAS USA* 81:461–465. Gastrin is thought to act only through the CCK-B receptor and not the CCK-A receptor. Mice with homozygous null alleles for either of the two CCK receptors, CCK-A and CCK-B, were used. It was found that the pancreatic morphology was normal in these knock out mice from 4 to 12 months of age. However, in the CCK-B receptor null mice the glucagon cells appear to have an increased relative volume. Since there may be a redundancy in these receptors, the double null mice were also examined and surprisingly, it was found that these mice also have normal pancreas morphology and beta cell mass. Thus, a third receptor has not been ruled out. These studies suggest that CCK is not a major stimulus for normal pancreatic growth and development.

Insulin and its Substrates:

There has been a recurrent question of whether insulin itself has an effect on the proliferation of pancreatic beta cells. The pancreas of mice with marked insulin resistance due to a null allele either of the insulin receptor, or of insulin substrate −1, or both were examined. These mice were found not to be diabetic. By quantitating the mass of β and non-β endocrine cells in these mice, it was found that a selective β-cell proliferation had occurred in these normoglycemic mice and that the beta cell mass reflected the degree of insulin resistance. While both IRS-1 +/− and insulin receptor +/− mice had both 2–3 fold increased plasma insulin and beta cell mass, those mice heterozygous for both null alleles had 10 fold increases of both. With further analysis, about 50% of the double heterozygous animals were diabetic when these were analyzed for β-cell mass. Surprisingly, the diabetic mice had β-cell mass 12–30 fold and much larger islets than the nondiabetic. These latter hyperinsulinemic mice had 3–5 fold increases as compared to wild type. These findings suggest that the potential for β-cell proliferation is not as limited as previously thought.

Another insulin substrate null mouse has also been studied, the IRS-2 knock out/null mouse. The IRS-2 knock out/null mouse shows hyperglycemia shortly after weaning. These mice have significant insulin resistance and β-cell mass only 40% that of wild type. This is in marked contrast with IRS-1 knock out mice that have more severe insulin resistance, double the β-cell mass and are normoglycemic. In addition, the IRS-2 null islets have appropriate secretion for their mass but are β-cell deficient even before birth. At 4 weeks of age, their β-cells incorporate the same or slightly more BrdU than either the wild type or the IRS-1 null mice, so there is no defect in their replicative ability. However, both at 18 day embryonic and day 2 postnatal, times of differentiation of ducts to islet, there are greatly increased numbers of apoptotic bodies in ductal tissue adjacent to islets, suggesting that IRS-2 may have a survival role in the newly differentiating islet cells.

Transcription Factors:

To understand the mechanism of pancreatic growth, various mice that are null or "knock out" for transcription factors found in islets have been studied. First, the hnf-1 (MODY 3) null mice were examined. Unlike the human counterparts, the heterozygote mice are normal functionally, however, the null mice are quite diabetic and have smaller islets with a decreased β-cell mass. The β-cells have a functional defect but cannot increase in mass adequately to compensate for this impairment. Second, the pdx-1 (PDX-1) heterozygote mouse was found to be diabetic even though it had no difference in β-cell mass from wild type, suggesting a functional defect rather than a defect in the mass of β-cells.

Markers Indicative of Expansion

Proliferation, e.g., rapid proliferation, of duct epithelial cells and/or exocrine cells can lead to the cells dedifferentiating back to a pluripotent state. Cells in this state are also referred to as dedifferentiated cells. Markers indicative of expansion can be used to detect cells in dedifferentiated state. Such markers can include cytokeratin, IPF-1 (PDX-1), Pref-1 and lack of insulin expression. The phenotype of duct cells after pancreatectomy (Px) can be observed to determine other markers which are indicative of this state.

In both in vivo in a PDX-1 heterozygous mouse model and in vitro with primary duct cultures, it was found that PDX-1 protein is transiently expressed in the newly replicated duct cells before their subsequent differentiation. PDX-1 positive cells are the precursor cells of the pancreas and the adult duct cells are facultative stem cells. Since the adult duct epithelium retains the ability to give rise to all the differentiated cell types of the pancreas, the question of the nature of the precursor cells is raised. Sustained proliferation of the ductal epithelium after partial pancreatectomy leads to an increased pool of less differentiated duct cells that serve as facultative stem cells and that these cells can then be stimulated to differentiate to mature islets and exocrine cells. These less dedifferentiated or protodifferentiated cells have lost their specialized functions of the mature duct cells and are referred to as dedifferentiated duct cells.

The precursor cells in the pancreatic duct have been characterized in three sets of experiments. First, the role of PDX-1 in the regenerating pancreas was examined. Using semi-quantitative RT-PCR, it was found that PDX-1 mRNA is expressed basally in the common pancreatic duct but it does not change during the ductal expansion after partial pancreatectomy inspite of a large increase in PDX-1 protein expression. Immunostaining for incorporated BrdU and PDX-1 was combined to understand if PDX-1 protein expression drove the expansion of the duct. Instead, it was found that replication precedes PDX-1 expression. During the period of 24–36 hours after Px, the epithelium of the common pancreatic duct has a burst of proliferation seen as a transient 3-fold increase of BrdU incorporation; by 48 hours after Px, the BrdU incorporation in this duct has returned to basal levels. Bonner-Weir et al. (1993) *Diabetes* 42:1715–1720. Yet in the first day after Px, little increase of PDX-1 protein levels was found in the common pancreatic duct by either Western blot or immunostaining. PDX-1 protein levels were only increased at 2–3 days after Px and returned to basal levels at 7–14 days after Px. The double immunostaining showed that initially the cells that incorporated BrdU did not express detectable levels of PDX-1 protein. In individual cells, BrdU incorporation preceded the expression of PDX-1 protein, but PDX-1 remained, at least transiently, in the duct cells after replication. At 3 days after Px when both immunostaining and protein levels of PDX-1 were markedly increased in these ducts, BrdU incorporation was low, indicating that the cells were now quiescent. Increased PDX-1 protein was seen following proliferation in the epithelium throughout the ductal tree. A similar pattern of transient protein expression is seen in primary duct cultures. This lag indicates that PDX-1 protein does not initiate regeneration and proliferation.

An intriguing finding was that BrdU was incorporated in cells before PDX-1 was detectable but that all obvious BrdU+daughter cells expressed PDX-1. Furthermore, this expression was transient. This turning on and then off of PDX-1 protein expression resembles what is seen in embryonic ducts. Most early embryonic duct cells express PDX-1 protein, but this protein is mostly lost in ducts in the days before birth. Guz et al. (1995 Development 121:11–18; Oster et al. (1998) J. Histo. Cyto. 46:707–715; Ahlgren et al. (1996) Development 122:1409–1416. It is important to remember that mature duct cells are both quiescent and have a differentiated phenotype with specific functions not seen in pancreatic exocrine or endocrine cells. Githens et al. (1988) J. Pediatr. Gastroenterol. Nutr. 7:486–506. Perhaps with the differentiation into a mature duct phenotype there is repression of the PDX1 protein expression, and conversely, with replication, a transient loss of this differentiation/repression. The regulation of PDX-1 protein expression may occur at the level of translational inhibition or at the level of protein stability. Translational inhibition is an important regulatory mechanism for controlling expression of genes during early development, in response to various stresses as well as for maintenance of metabolic homeostasis; such inhibition can be mediated by a regulatable repressor. Richter et al. (1991) Bioessays 13:179–183; Standart et al. (1994) Biochim. 76:867–879. Since differentiation is such a complex event, any regulatable repressor factor may affect the translation of many different proteins in a cascade and the effect on PDX-1 may only be indirect. PDX-1 protein may, or may not, be causative in the dedifferentiation. Indeed, PDX-1 may only be a marker of this state. PDX-1+ duct cells transiently regain their pancreatic pluripotency and thus can be considered facultative stem cells.

The regulation of PDX-1 protein expression may occur at the level of translational inhibition or at the level of protein stability. Translational inhibition is an important regulatory mechanism for controlling expression of genes particularly during early development. PDX-1 protein may, or may not, be causative in the dedifferentiation; indeed, PDX-1 may only be a marker of this state.

To further characterize post-transcriptional regulation of PDX-1 expression, transgenic mice can be used that are heterozygous for a PDX-1: GFP transgene generated. In these mice, GFP is cloned 20 bp upstream from translation start site of PDX-1. Hence, GFP transgene is transcribed from PDX-1 transcriptional start site and contains most of the 5' untranslated region. A partial pancreatectomy on 6 week old mice has the same pattern of ductal expansion forming focal regions of regeneration that then differentiate into islet, exocrine and duct tissue as documented in the rat. Six week old mice can undergo partial pancreatectomy or sham Px (3 each group). The mice are given BrdU (5-bromo-2'deoxyuridine, Sigma, 100 mg/kg body weight intraperitoneally) 6 hours before their sacrifice, and are sacrificed by overdose anesthesia (Nembutal) at 40 hours after surgery. From one group of Px and sham animals, pancreas can be excised, fixed in 4% (para) formaldehyde, and embedded in paraffin. Adjacent sections are stained for double immunofluorescence for BrdU and PDX-1, for GFP and BrdU using rabbit anti-GFP antibody (8363-2, Clontech), and for GFP and PDX-1. In a second set of animals, duct for RNA extraction can be isolated. The RNA is analyzed by multiplex RT-PCR with primers for PDX-1 and GFP to confirm that in mice, as in rats, PDX-1 transcription is unchanged after surgery and that the transgene is regulated similarly to native PDX-1.

If the 5'untranslated region of the PDX-1 gene is required for posttranscriptional regulation, co-induction of GFP and PDX-1 proteins is expected. If the 5' untranslated region is not required, GFP protein, but not PDX1 protein, should be expressed in the common pancreatic ducts before replication (i.e., sham), confirming that PDX-1 mRNA but not protein is expressed in the quiescent adult duct and at 40 hours both GFP and PDX-1 should be expressed in the majority of cells.

To show that the protein is lost in cells that had expressed it, common pancreatic ducts can be isolated from 4 other unoperated mice and cultured on Matrigel coated dishes. Dishes are fixed with 4% (para) formaldehyde at 24, 36, 48, and 72 hours for 30 minutes, washed and then stained immunofluorescently for PDX-1. GFP has been found to still have its fluorescence after this treatment, however if it is not bright enough GFP for photography, the GFP can be immunostained. In cultured rat ducts at 24 and 48 hours, all cells in a plaque express PDX-1 protein, but by 72 hours, only the peripheral recently replicated cells do. These in vitro and in vivo experiments can be used to determine if the regulation of PDX-1 in ducts is post-transcriptional.

Pref-1, a glycoprotein found in mice and rats, is homologous to the delta-like protein (dlk) of human and Delta of Drosphilia; fetal antigen-1 (FA-1) is identical to the extracellular domain of Pref-1/dlk. Palder et al. (1998) *Endocrinol.* 139:3316–3328 . The transmembrane Delta family acts as ligands for Notch proteins/receptors on neighboring cells and in doing so transmit an intracellular signal cascade in those Notch expressing cells to suppress differentiation. Lendhal et al. (1998) *Bioessay* 20:103–107. In fact, Pref-1 expression is thought to maintain a dedifferentiated state, being down-regulated during adipocyte differentiation and at an early stage of adrenocortical regeneration. Halder et al. (1998) *Endocrinol.* 139:3316–3328. However, its role must be more complex since both in the pancreas and the adrenal gland, Pref-1 protein is downregulated in some differentiated cell types (pancreatic duct, adrenal cortex) but maintained in others (beta cells/islets, adrenal medulla). In the pancreas FA-1/Pref-1 protein was shown to be expressed by most of the non-endocrine parenchymal cells (i.e., duct epithelium) early in development but gradually to disappear from these cells and become restricted to the beta cells. Tornehave et al. (1996) *Histochem. & Cell Biol.*

106:535–542. This pattern of expression is similar to that of PDX-1. Guz et al. (1 995) *Development* 121:11–18; Oster et al. (1998) *J. Histo. Chem.* 46:707–715. However in preliminary data, it was found by RT-PCR analysis that Pref-1 mRNA is expressed in isolated pancreatic ducts from unoperated adult rats, even though these ducts are said to be devoid of FA1/Pref-1 protein. Tornehave et al. (1996) *Histochem. & Cell Biol.* 106:535–542; Carlsson et al. (1997) *Endocrinol.* 138:3940–3948. Additionally, because Pref-1 gene expression has been shown to be stimulated via one of the family of EGF receptors, ErbB3 (although not by EGFR) and EGFR ligands have been shown to stimulate pancreatic duct proliferation, Pref-1 may be expected to increase after ductal proliferation.

It appears that Pref-1 protein expression in ducts may also mark undifferentiated pluripotent duct cells and be expressed transiently after Px. To test this hypothesis, semi quantitative RT-PCR analysis can be run for Pref-1 using the primers:

5'CCTTGTGCTGGCAGTCCTTTCC (SEQ ID NO:7)
3'TCTGTGAGGCTGACAATGTCTGC (SEQ ID NO:8)

for rat Pref-1 with a-tubulin for an internal control for samples from isolated common pancreatic ducts from rats 4, 12, 24 hrs and 2, 3, 7 days after Px and sham Px surgery as well as unoperated controls. Standardized conditions for linear amplification for this set of primers has already been prepared using techniques as in our previous studies. In parallel, immunostain for Pref-1/FA-1 can be performed using an anti-Pref-1 antibody. The advantage of the RT-PCR for the initial screening is that much information can be gleaned from a small amount of tissue or one experiment. The disadvantage is that heterogeneity is not accounted forand that only a few cells that are strongly positive for a gene may give a false interpretation. The second tier of analysis, immunostaining, overcomes these problems of interpretation of RT-PCR. Particular attention can be given to Pref-1 protein expression in the common pancreatic ducts and in the ductules in the focal areas of regeneration. If the expression pattern resembles that of PDX-1, then double immunostain for PDX-1 (nucleus) and Pref-1 (plasma membrane/cytoplasm) can be performed to confirm whether there is co-localization. It is unclear from the previous reports if Pref-1 is regulated at the transcriptional or post-transcriptional level. If it is, various mammalian members of the Notch family can be screened using RT-PCR.

Transplantation into Vertebrate Animals

For transplantation, animals can be anesthetized with Metofane and a lumbar incision can be created through which the left kidney is exteriorized. The cell aggregates are quickly inserted under the kidney capsule, the kidney repositioned and the incision stapled close. Tail bleeding for glucose monitoring is similar to finger pricks in humans; an animal is lightly restrained in a cloth towel and the tip of the tail is snipped with sharp scissors. Only 50 µl of blood is usually taken and the cut clots rapidly. For all other surgical procedures animals can be anesthetized with Nembutal.

For pancreas excision for islet or duct isolation or histology or RNA extraction, the animal can be overdosed, and then the pancreas can be removed, e.g., a pneumoth orax can be performed. For partial pancreatectomy, rats can be anesthetized with 30 mg/kg Nembutal. The abdomen is then shaved and cleaned with ethanol and a midline incision is made. Partial pancreatectomy is accomplished by abrading the tissue from intact blood vessels. The mesenteries attaching the pancreas to the spleen and colon are disengaged. Only a defined proportion of the pancreatic tissue is removed (90%); none of the other organs are compromised. The abdomen is sutured close, antibiotics are put on the wound and the skin is stapled close. Saline for rehydration is administered subcutaneously at the scapular region.

Pharmaceutical Compositions & Administration of Pancreatic Islets

Common methods of administering pancreatic cells to subjects, particularly human subjects, are described in detain herein. For example, pancreatic cells can be administered to a subject by injection or implantation of the cells into target sites in the subjects. In addition, the cells can be inserted into a delivery device which facilitates introduction by injection or implantation of the cells in the subjects. Such delivery devices include tubes, e.g., catheters for injecting cells and fluids in to the body of a recipient subject. In a preferred embodiment, the tubes additionally have a needle, e.g., a syringe, through which the cells of the invention can be introduced into the subject at a desired location. The pancreatic cells can be inserted into such a delivery device, e.g., a syringe, in different forms. For example, the cells can be suspended in a solution or embedded in a support matrix when contained in such a delivery device. As used herein the term "solution" includes a pharmaceutically acceptable carrier or diluent in which the cells of the invention remain viable. Pharmaceutically acceptable carriers and diluents include saline, aqueous buffer solutions, solvents and/or dispersion media The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal and the like. Solutions of the invention can be prepared by incorporating the pancreatic cells described herein in a pharmaceutically acceptable carrier or diluent and as require other ingredients enumerated above, followed by filtered sterilization.

Support matrices in which the pancreatic cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from mammal, and collagen matrices. Synthetic biodegradable matrices include synthetic polymers such as polyanhydrides, polyorthoesters, and polylactic acid. Other example of synthetic polymers and methods of incorporating or embedding cells into the matrices are known in the art. See e.g., U.S. Pat. No. 4,298,002 and U.S. Pat. No. 5,308, 701. The matrices provide support and/or protection for the fragile pancreatic cells in vivo.

The terms "introduction," "administration", and "transplantation" are used interchangeably herein and refer to delivery of cells to a subject by a method or route which delivers the cells to a desire location. The term "treating" as used herein includes reducing or alleviating at least one adverse effect or symptom, e.g., absolute or relative insulin deficiency, fasting hyperglycemia, glycosuria, development of arteriosclerosis, mocroangiopathy, nephropathy, and neuropathy, of diseases characterized by insufficient insulin activity. As used herein, the language "diseases characterized by insufficient insulin activity" include diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of β cells as in IDDM (Type I diabetes), secretion, such as impairment of insulin secretory responses as in NIDDM (Type II diabetes), the form of the insulin molecule itself, e.g., primary, secondary or tertiary structure, effects of insulin on target cells, e.g., insulin-resistance in bodily tissues, e.g., peripheral tissues and responses of target cells to insulin.

Common methods of administering pancreatic cells to subjects, particularly human subjects, include implantation of cells in a pouch of omentun (Yonda, K et al. (1989) *Diabetes* 38 (Suppl. 1): 213–216), intraperitoneal injection of the cells, (Wahoff, D. C. et al. (1994) *Transplant. Proc.* 26:804), implantation of the cells under the kidney capsule of the subject (See, e.g. Liu, X. et al. (1991) *Diabetes* 40:858–866; Korgren, O. et al. (1998) *Transplantation* 43(3): 509–514; Simeonovic, D. J. et al. (1982) Aust. *J. Exp. Biol. Med. Sci.* 60:383), and intravenous injection of the cells into, for example the portal vein (Braesch, M. K. et al. (1992) *Transplant. Proc.* 24(2): 679–680; Groth, C. G. et al. (1992) *Transplant. Proc.* 24(3): 972–973). To facilitate transplantation of the pancreatic cells under the kidney capsule, the cells can be embedded in a plasma clot prepare from, e.g., plasma from the recipient subject (Simeonovic, D. J. et al. (1982) Aust. *J. Exp. Biol. Med. Sci.* 60:383), or a collagen matrix. Cells can be administered in a pharmaceutically acceptable carrier or diluent as described herein.

EXAMPLES

Materials and Methods

Initial Tissue and Culture Conditions:

Human islet isolations were performed in the Islet Core Laboratory of the JDF Center for Islet Transplantation at Harvard Medical School using the method described in Linetsky et al. (1997) *Diabetes* 46:1120–1123. After purification on a Ficoll gradient, the top interface (1.062/1.096 densities) was 50–95% islet with varying amounts of duct and degranulated acinar tissue, the middle interface (1.096/1.11 densities) contained 1–15% islets, duct and degranulated acini, and the pellet was mostly well granulated acinar tissue with less than 1% islets. In the top and middle layers there were sheets of ductal epithelium from larger ducts whereas the clumps of exocrine cells found in all layers consisted of small intercalated ducts continuing into the acini. From 8 collagenase (Liberase, Roche) digested pancreases (donor age 27–59 years), tissue from these layers was cultured in 50 ml CMRL 1066 (5.6 mM glucose) media plus 10% fetal bovine serum in Falcon non-treated T-75 flasks (#3012 Becton Dickinson) at 37° C., 5% $CO_2$. At 1–4 days the non-adherent tissue (both viable and dead) was removed with a media change, and the adherent, or residual, cells were expanded for up to 1 week with additional media changes every 2–3 days. At about 1 week, when most, if not all, adherent cells were in monolayer, the media was changed to 20 ml serum-free DMEM/F12 (8 mM glucose) medium with 1 g/L ITS supplement (5 mg/L insulin+5 mg/L transferrin+5 mg/L selenium, Sigma), 100 U/ml penicillin, 100 μg/ml streptomycin, 2 g/l BSA, 10 mM nicotinamide and keratinocyte growth factor (KGF)(10 ng/ml, Roche). It was found that DMEM/F12 (8 mM glucose, plus nicotinamide) facilitated growth of rat and pig duct cells in vitro. KGF has been reported to be a duct mitogen (Yi et al. (1994) *Am. J. Pathol.* 145:80–85), and it had been found it to stimulate ductal proliferation in vitro without evident changes in cell phenotype. These cells were then grown for about 1–2 week until reaching near confluence or forming substantial plaques of epithelial cells. The cells were then layered with Matrigel™, commercial preparation of murine basement membrane (Collaborative Research—Becton Dickinson, Lexington Mass.) as per instructions of supplier for thin layer gel with the exception of an increased gelling time at 37° C. Briefly, the cells were coated with 50 μl Matrigel™ per $cm^2$ and allowed to gel overnight before additional media was added. Cell samples were taken at different time points over the course of 6 weeks. Dithizone (diphenylthiocarbozone), which stains insulin-containing cells bright red, was used to assess quickly the presence of insulin-producing cells.

Tissue Fixation and Immunochemistry

Monolayer cultures were fixed for 30 min in either 4% (para) formaldehyde in 0.1M phosphate buffer (PFA) or in Bouin's solution, and then rinsed in the phosphate buffer. Three dimensional structures (cysts) that formed from these monolayers were harvested by mechanical shearing with a stream of media. Harvested cysts were fixed in PFA for 60 min, enrobed in 2% agar to keep the pellet together through processing and embedding, immersed in the same fixative for another 90 min, washed, and stored in 0.1M phosphate buffer until routine embedding in paraffin; sections of these were used for immunostaining. Other cysts were fixed in 2.5% glutaraldehyde 0.1 M phosphate buffer for 2 hr, washed and stored in phosphate buffer until being embedded in plastic resin (Araldite) for semithin (1 μm) sections or ultrathin sections for ultrastructural analysis.

Double immunofluorescent staining were done sequentially using primary antibodies made in different species: Guinea pig anti-human insulin (1:200, Linco Research Inc. St. Charles, Mo.), rabbit anti-bovine glucagon (1:2000, kindly donated by Dr. M Appel, University of Massachusetts Medical School, Worcester, Mass.) and rabbit anti-bovine pancreatic polypeptide (1:3000, gift of Dr. R. E. Chance, Eli Lilly, Indianapolis, Ind.), rabbit anti-synthetic somatostatin (1:300, made in our own laboratory), a cocktail of the latter 3 antibodies (anti-glucagon, -somatostatin and -pancreatic polypeptide) for identifying the non-β islet cells (17); monoclonal mouse anti-human cytokeratin 19 (CK 19) antibody (1: 100, Dako, Glostrup, Demnark)(18)or rabbit pancytokeratin (1: 100, Dako ); IDX-1 antibody (Hm-253, dilution 1:500 from Dr. J. Habener, Massachusetts General Hospital, Boston, Mass.)(19). The conjugated secondary antibodies used for immunofluorescence were Texas Red conjugated donkey anti-Guinea pig IgG, FITC conjugated donkey anti-rabbit IgG and streptavidin conjugated FITC (1:100 dilution for all, Jackson Immuno-Research Lab., West Grove, Pa.). Biotinylated horse anti-mouse IgG and normal horse serum were purchased from Vector Inc. (Burlingamne, Calif.). For cytokeratin and IDX-1 staining of sectioned, tissue antigens were retrieved by microwaving in citrate buffer (3 times of 4 min each with the maximum strength of a domestic microwave) (20). Monolayer cultures were incubated for 10–20 minutes in 0.3% Triton X-100 (Fisher) with 1% lamb serum (Gibco BRL) before primary antibody incubation.

Insulin and DNA Content

Harvested cysts or cells removed from flasks by treatment trypsin/EDTA (1× trypsin-EDTA solution, Cellgro, Mediatech; 10–15 min at 37° C.) were brought up to 1 ml high salt buffer (2.15 M NaCl, 0.1 M $NaH_2PO_4$, 0.04 M $NaHPO_4$, EDTA, pH 7.4) and then were sonicated 3 times, 10 seconds each at 4–6 watts and then stored at −20° C. until assayed. Insulin was measured using a radioimmunoassay kit for human insulin from Linco. DNA content was measured fluorometerically using Hoechst 33258 dye as described by DyNA Quant (Hoefer Pharmacia Biotech Inc, San Francisco Calif.).

RNA Extraction and Analysis:

Total RNA from samples was extracted following manufacturer suggested protocols using Ultraspec (Biotecx Laboratories, Houston, Tex.). cDNA synthesis was performed as previously described in Sharma et al. (1999) *Diabetes* 48:507–513. Polymerase chain reaction (PCR) was carried out in 50 µL reactions using 3 µL of the diluted cDNA reaction product (corresponding to 20 ng RNA equivalent) as template mixed with 47 µL of PCR mix (1× Taq buffer (Promega), 1.5 mM $MgCl_2$ (Promega), 10 pm of each insulin primers (forwards and backwards) (Genosys, The Woodlands, Tex.), 4 µl of 4:6 ratio of 18S primers: competimers (Classic 18S Internal Standards, Ambion, Austin Tex.), 80 µM cold dNTPs (Gibco/BRL), 5 U AmpliTaq Gold DNA polymerase (Perkin-Elmer), and 2.5 µCi [$\alpha^{32}P$] dCTP (New England Nuclear, Boston, Mass.)). RT-PCR for insulin with 18S ribosomal subunit as internal control was run on the samples. Primers were as follows: human insulin 5': TCA CAC CTG GTG GAA GCTC (SEQ ID NO:1); human insulin 3': ACA ATG CCA CGC TTC TGC (which yield a 179 bp PCR product) (SEQ ID NO:2); and for internal control 18S primers: competimers (Classic 18S Internal Standards (which yield a 488 bp PCR product).

The thermal cycling protocol began with a denaturing step of 97° C. for 10 minutes, then 19 cycles of (94° C. 1 min, 55° C. 1 min, 72° C. 1 min), and finished with 72° C. for 10 minutes.

For human glucagon, the following primers were used: 5'ATG AAC GAG GAC AAG CGC (SEQ ID NO:3); 3':TTC ACC AGC CAA GCA ATG (SEQ ID NO:4) (which yields a 236 bp product); and human cyclophilin 5': CCC ACC GTG TTC TTC GAC (SEQ ID NO:5), 3':ATC TTC TGC TGG TCT TGCC (SEQ ID NO:6).

The reaction volume differed from that above in that 7.5 pmol of each glucagon primer and 25 pmol of each cyclophilin primers were used; the thermal cycle profile was the same except that 23 cycles were used and the annealing temperature was 59° C. Screens were scanned using a Molecular Dynamics Storm Phosphorimager and reaction products were quantitated with ImageQuant software (Molecular Dynamics, Sunnydale, Calif.). Results are calculated as a percentage of internal standard and presented as mean±SEM. Reaction conditions were standardized so as to observe linear amplification of PCR products (for both insulin and ribosomal 18S, glucagon and cyclophilin) for different amounts of cDNA (10–50 ng RNA equivalent) and cycle numbers (18–32 cycles). Graded dilutions (1–20%) of a human islet preparation (H99-22, 90% islet purity, 676 ng insulin/µg DNA) were run to establish a standard curve of insulin mRNA to 18 S mRNA and of glucagon mRNA to cyclophilin mRNA. By including 2 samples from this curve as standards in any other RT-PCR experiment, an estimate of the % islet for a sample could be made.

Insulin Secretion:

Three dimensional structures (cysts/CHIBs) from one to two flasks of tissue from pancreas 19, 24 and 25 were harvested at 3–5 weeks culture and washed three times in RPMI (5 mM glucose, 10 mM HEPES, pencillin/streptomycin, 5% fetal bovine serum). From each flask, 12 aliquots of 40 cysts/CHIBs were incubated in 1.5 ml of the same media in 12 well plates for 4 hours at 37° C., the media was removed for measurement of preincubation insulin levels, and fresh media was added for a 24 hr incubation. Following this 24 hrs period, media was again removed and measured for basal insulin secretion, and fresh media with either 5 mM or 20 mM glucose was added. At the end of this second 24 hr incubation, the final media was removed for measurement with a human insulin radioimmunoassay kit (Linco).

Results

To promote the attachment of duct cells rather than islet cells, non-sticky culture flasks were used. These flasks have been used to maintain islets in suspension. With pure islet preparations obtained from the top layer of the density gradient, little tissue became adherent even with 7 days culture. It was noted, however, that clumps of non-islet tissue obtained from the top, middle or pellet layers can adhere to this non-sticky surface starting at about 24 hr. It was mainly in the less pure islet preparations that there were adherent cell clumps within 2–4 days. While there was considerable loss of floating tissue as has been reported for pancreatic acinar tissue in culture, the quantity of cell clumps that adhered increased with time. If the non-adherent clumps were removed when the adherent density reached an empirically determined level (covering about 10% of surface), the adherent cells had little to no dithizone staining and included few fibroblasts. Initial samples for insulin and DNA contents were taken at the removal of non adherent tissue and before the clumps flattened into monolayers. The adherent tissue was only 2.5 –24% of the original DNA and 2.5–11% of the original insulin content (See Table 1). However, if the non-adherent tissue remained longer in the cultures, both the amount of adherent islet tissue (dithizone positive) and fibroblasts increased (data not shown). With additional time, cells grew from the adherent clumps and formed monolayer plaques of cells with clear epithelial morphology.

Once the clumps had attached and formed monolayers, the media was changed to serum free media with added growth factor (KGF) in order to favor stimulation of ductal epithelial growth over that of fibroblasts. Over the next 5–10 days the plaques of epithelial cells became nearly confluent. Most of these cells were immunopositive for cytokeratin (results using anti-cytokeratin 19 and anti-pan-cytokeratin were identical ), and varying numbers were also IPF-1 (PDX-1/IDX-1/STF-1) positive. The occasional insulin positive β cells had strong IPF-1 nuclear staining. In addition many duct cells expressed this transcription factor, both in the nucleus and in the cytoplasm. Scattered cells, both singly and in patches, had cytoplasmic IPF-1 staining with little nuclear staining and again no insulin staining. The large, cytokeratin positive cells in cobblestone patterns are characteristic of pancreatic ductal epithelium. Islets that were included flattened into clusters of small epithelial cells without cytokeratin 19 staining. At the stage of 75–90% confluency, the cultured cells were overlaid with the matrix.

Figure 1C:
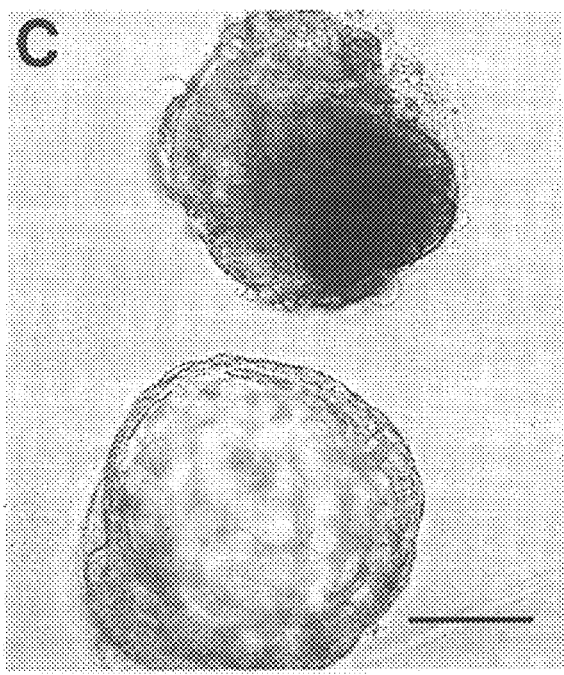
Figure 1D:
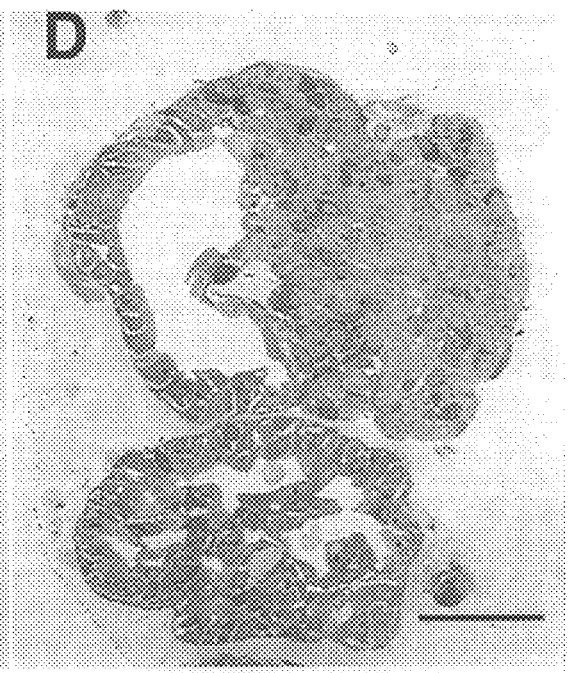
FIG. 1D shows the structure of budding islet cells from a cyst in a toluidine blue 1 μm section. Magnification bar of FIG. 1B is 500 μm.

During the first 1–2 weeks with Matrigel, there was movement of the epithelial cells into three dimensional cystic structures, ranging 50–400 µm in diameter, which often had multiple buds of dithizone positive cells (See FIG. 1). These structures, termed CHIBs (cultivated human islet buds), were observed in cultures from all layers and all 8 pancreases. The frequency of cysts/CHIBs appeared to be more dependent on extent of epithelial confluency than on the layer or pancreas of origin. Control flasks without the matrix overlay produced few, if any, cystic structures but in some preparations some solid spheres formed from the monolayer.

There was significant increase of both the cultured tissue and its insulin content during the 3–6 weeks culture (last 2–3 weeks with Matrigel). Data from the 3 pancreas from which samples of the fill content of 75 $cm^2$ flasks were taken initially and at several intermediate time points are shown in Table 1 below.

TABLE 1

Insulin and DNA content of 75 cm² flask containing cultured human ductal cells

| | Percent Islets | Original Aliqout (50 ml) | Initial Adherent | 2 weeks | 3 weeks | 4 weeks |
|---|---|---|---|---|---|---|
| H99-13 | 58% | | | | | |
| Insulin (ng) | | 3200 | 78.4 | — | 888 | — |
| DNA (μg) | | 160 | 3.8 | — | 22.1 | — |
| Insulin/DNA (ng/μg) | | 20 | 20.5 | — | 40.2 | — |
| H99-19 | 5% | | | | | |
| Insulin (ng) | | nd | 70.8 | 123 | 344 | 868 |
| DNA (μg) | | nd | 30.7 | 39.8 | 29.8 | 41 |
| Insulin/DNA (ng/μg) | | | 2.3 | 3.1 | 11.5 | 21.1 |
| H99-20 | <5% | | | | | |
| Insulin (ng) | | 1600 | 174 | — | 1788 | 2564 |
| DNA (μg) | | 250 | 60 | — | 42.9 | 46.8 |
| Insulin/DNA (ng/μg) | | 6.4 | 2.9 | — | 41.2 | 54.8 |

At 2–4 d after islet isolation the majority of the tissue aliquot originally placed into the culture flask was removed, leaving only the tissue adhering to the non-treated surface. Much of the original tissue died as would be expected for acinar tissue. The cell clumps spread to form monolayers; at 2–3 weeks, these monolayers were coated with a thin Matrigel layer.
nd: not determined.

The insulin to DNA ratio of the starting adherent material (8.2±4.2 ng insulin/μg DNA) was 1–2% that of the islet preparations whether using the mean values from the 4 purest human islet preparations (top layers) to date (90±2% islet purity, 920±170 ng insulin/μg DNA) or of the purified islets (top layers) from 4 pancreases of Table 2 (75±4% islet purity, 380±130 ng insulin/μg DNA). Over the 3–4 weeks culture period the insulin to DNA ratio per flask increased, but more importantly the insulin content per flask increased 10–15 fold while the DNA content increased 0.8–7 fold. In contrast the cultured tissue from the pellet layers showed increases in insulin: DNA ratios but had no increase in insulin and considerable loss of DNA (starting: 63±52 ng insulin, 64.7±13.6 mg DNA n=3, 3–4 wk: 50±10 ng insulin, 24.4±4.2 mg DNA, n=3). However, dithizone positive CHIBs were formed from these cultures of pellet tissue.

After 2 weeks of matrix overlay, cysts/CHIBs would lift off with the mild agitation of media changes. Others were harvested at the end of the experiment by mechanical shearing with a forceful stream of media. However, this harvesting was imprecise leaving some CHIBs still attached and lifting off some of the simple ductal cysts as well as some of the remaining monolayer or "lawn". As shown in Table 2, the cysts/CHIBs were enriched in insulin. There was considerable variation in this enrichment with various batches of cysts/CHIBs even from the same pancreas and the same time period, partly due to the imprecision of shearing.

TABLE 2

Enrichment of Insulin Content in cysts/CHIBs

| Sample | Layer | Insulin/DNA (ng/μg) Individual Samples | Insulin/DNA (ng/μg) Mean ± sem |
|---|---|---|---|
| H99-08 | Top | 852, 333, 249, 327 | 440 ± 139 |
| H99-10 | Top | 48, 66 | 57 |
| H99-12 | Top | 149, 61, 149 | 120 ± 29 |
| H99-13 | Top & Middle | 178, 218, 68 | 154 ± 45 |

TABLE 2-continued

Enrichment of Insulin Content in cysts/CHIBs

| Sample | Layer | Insulin/DNA (ng/μg) Individual Samples | Insulin/DNA (ng/μg) Mean ± sem |
|---|---|---|---|
| H99-19 | Middle | 48, 110 | 78 |
| H99-20 | Middle | 110, 152, 94, 27, 74 | 91 ± 21 |

Starting at 10 days after Matrigel, some cysts/CHIBs could be collected after becoming dislodged during media changes. Other samples were harvested at the end of an experiment by mechanical shearing. The time of culture for the cysts/CHIB samples were between 5–6 weeks (range 27–65 days) after isolation, 2–3 weeks after Matrigel (range 10–41 days).

Demonstration that the insulin was produced by the tissue and not just adsorbed from the media was confirmed by three approaches: dithizone staining, immunofluorescent staining of the cysts/CHIBs and semiquantitative RT-PCR for insulin. The CHIBs were composed of cytokeratin 19 positive duct cells and hormone positive islet cells. The CHIBs were found to be positive for insulin and for non-β cell hormones including glucagons, somatostatin and pancreatic polypeptide. As even suggested by the dithizone stained samples (as shown already in FIG. 1), the proportion of endocrine tissue in the cysts/CHIBs varied among the different pancreas; many were simple ductal cysts while others were cysts with multiple islet buds. The non-β endocrine cells were often equal in proportion to the β cells. A few cells with double staining for insulin and the non β cell hormones suggested that some endocrine cells were immature and still in the process of differentiation. Many of the cells within CHIBs had clearly differentiated phenotypes by ultrastructural analysis; both endocrine and mature duct cells were identifiable, however, some cells that had left the ductal epithelium were not granulated.

The analysis of mRNA by RT-PCR showed initially very low levels of insulin mRNA in the starting material but increases were found as CHIBs developed. Using the standard curve of insulin mRNA: 18S mRNA for different dilutions of purified islets, the initial insulin mRNA levels were the equivalent of 0.9±0.4% islet (n=6, all middle layers) while, from pancreas H99-20, 5.9% islet at 4 weeks and 5.0% islet in cysts/CHIBs. Similarly, glucagon mRNA levels increased from the initial adherent tissue being equivalent of 1.3±0.7% islet and harvested CHIBs being 14.1±7.2% islet and remaining lawn 4.8±0.8% islet (n=3).

Figure 2:
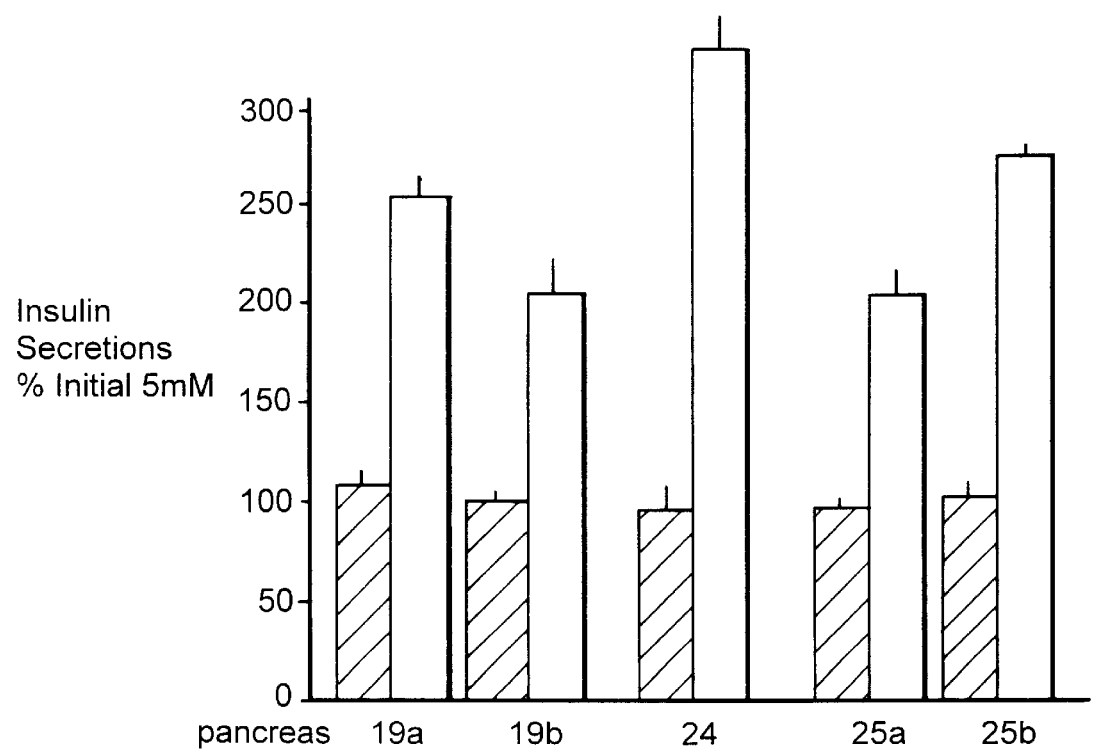
FIG. 2 is a graft depicting the responsiveness of cysts/CHIBs to glucose in in vitro secretion studies. Middle layer tissue from two flasks of pancreas H9-19 (19a & 19b) and H99-25 (25a & 25b) and one flask of pancreas H99-24 (24) are shown. After an initial 4 hours preincubation, each sample was incubated for 24 hours in RPMI with 5 mM glucose to determine basal secretion levels. Media was then supplemented with either 5 mM (hatched) or 20 mM (solid) glucose for a 24-hour period. Insulin secretion is expressed as a percentage of the same tube basal levels.

Studies were performed to determine whether the new β cells in these CHIBs could secrete insulin in response to glucose. To address this question, insulin secretion was studied over sequential and parallel 24 hr time periods (See FIG. 2) in tissue from three pancreases. The data from each pancreas were qualitatively the same. There were no differences in insulin concentration in the basal samples at 5 mM glucose for either the first or second 24 hr period (pancreas 19: 1st: 1.8±0.1 ng/ml, n=24 replicates; 2nd: 1.8±0.1 ng/ml, n=12 replicates). However in those samples exposed to a stimulatory 20 mM glucose during the second 24 hour period, there was a 2.4 fold increase in insulin (pancreas 19: 4.3±0.5 ng/ml, n=12 replicates), demonstrating the glucose responsiveness of the CHIBs.

Discussion

Human duct tissue was successfully expanded and then to direct its differentiation to islet endocrine cells in vitro. The ability to cultivate human islets in vitro from digested pancreatic tissue that is usually discarded after islet isolation opens a new approach for β cell replacement therapy. Human islet isolations yield at best only 400,000–600,000 islets, which means that more than one donor may be required for a successful transplant. Hering et al. (1999) *Graft* 2:12–27. As reported here, insulin content was increased 10 to 15 fold and the endocrine tissue became organized into islet-like structures consisting of β and non-β endocrine cells. These experiments were designed to start with the non-islet ductal tissue with no effort made to salvage islet tissue from the non-islet layers. In fact because islets rarely adhere to the non sticky flasks, the conditions did not favor their inclusion. This data provide evidence of the potential to expand and differentiate human duct cells to islet cells.

These conditions may be further optimized by, for example, further expansion of the ductal tissue or higher efficiency in differentiating cells. Being able to use the pellet layer with higher efficiency would be particularly advantageous because this layer often contains 2–3 times more tissue than the middle layer. It is puzzling why the cultures of pellet layer had the same growth appearance (cobblestone plaques) and morphogenesis as the middle layer but had no increase in insulin content after application of the Matrigel. The adherent starting tissue was for the most part ductal epithelium, no matter which purification layer was being used. There were some fibroblasts, but the growth conditions favored the epithelial cells. The only noticeable difference in these two layers initially was that the middle had more sheets of duct epithelium from larger ducts while the pellet layer had mostly exocrine clumps consisting of small intercalated ducts continuing into acini. It is entirely possible that the cells from the smaller ducts/acini have less capacity to differentiate into endocrine cells.

The adherent cells during the early culture period seem to be ductal cells. The large cytokeratin positive cells that form in cobblestone pattern are characteristic of pancreatic ductal epithelium. These large cells often had cytoplasmic and/or weak nuclear staining for the transcription factor, IPF-1. In contrast, β cells were small in size, cytokeratin negative and insulin positive by immunostaining and had strong nuclear staining for IPF-1. While this transcription factor has been mainly localized to the embryonic duct cells and to the islet cells, particularly the β and some delta cells (Guz et al. (1995) *Development* 121:11–18), it was found that in the adult rat recently replicated duct cells also transiently express this protein in the nuclei (Cobb et al. (1995) J. Biol. Chem 270:14843–14846). In these human cultures, the pattern of IPF-1 protein was variable but consistent with recent proliferation of the cells.

There are several lines of evidence supporting that islets are not a major component of the initial adherent cultures. First, there was little dithizone staining of the adherent cells, even from the tissue aliquots from the top layers in which the islets in suspension were strongly stained by dithizone. This is not unexpected since these non-treated flasks had been chosen originally to maintain isolated islets in suspension. In fact, the purer preparations had little adherent tissue; it was when the islet purity was lower (equal or less than 75%) that an appreciable amount of adherent tissue was found. Second, the initial insulin to DNA ratio was less than 2% that of our purest human islet preparations. Since the initial samples for insulin (at 2–4 days) were taken before there was much spreading or replication of the tissue and the suspended islets maintained their insulin content, it is unlikely that adherent islets had lost all their insulin or became dedifferentiated. This is consistent with the low levels of insulin mRNA found in these early cultures. To obtain further insight into how many islets might have adhered in the early stages of culture, purified islets of pancreas H99-20 were extracted for insulin and DNA determination, with the finding of 5 ng insulin and 6.5 ng DNA per islet, indicating that each islet consisted of about 930 cells. The amount of insulin contained in the adherent tissue of a single flask from this pancreas was 174 ng, which is the equivalent of 35 islets. These 35 islets would contain 228 ng DNA which was 0.4% of the total from the adherent cells of the flask. After 8 days of Matrigel treatment, a flask that started with an identical aliquot of tissue contained 2560 ng insulin or the equivalent of 512 islets or 7.1% of the final tissue. This is a 15 fold expansion.

While theoretically it is possible to have increased insulin content and increased insulin-containing cells from replication of the few beta cells that were in the initial adherent cell population, this is unlikely for several reasons. First, human beta cells have been shown to have extremely low replication rate (less than 0.1% labeling for Ki67, a protein present in most cells that are in the cell cycle since it is expressed from mid G1 through mitosis). This low level of replication was shown also in late fetal (Bouwens et al. (1997) *Diabetologia* 40:398–404) and adult pancreas (Bouwens et al. (1998) *Diabetologia* 41:693–633) as well as islet preparations that were cultured with HGF and on extracellular matrix (Lefebvre et al. (1998) *Diabetes* 47:134–137). Second, there is a parallel enrichment of glucagon during the culture as seen by the immunostaining and the RT-PCR. Third, the pattern of budding of islet tissue is highly similar to that of in vivo neogenesis with the mix of β and non β endocrine cells with immature endocrine cells as illustrated by both colocalization of islet hormones and ultrastructurally "undifferentiated" cells seen between the duct and endocrine cells. Additionally the glucose-induced insulin response is immature as one would expect from newly formed islets. Thus, this data strongly favor neogenesis of islet tissue from ductal cells.

Other Embodiments

Optimizing Culture Conditions for Expansion:

Additional approaches can be taken to further optimize the culture conditions for dedifferentiation of pancreatic cells and differentiation of dedifferentiated cells. Such approaches may include one or more of the steps set forth below:

Isolated pancreatic ducts can be treated with PBS with 1 mM EDTA and 0.25% trypsin for 10–15 min at 37° C. to disperse the cells (at least into clumps smaller than can be minced), with mild trituration up and down a pipette tip. A similar procedure has been used for mammary ducts, lung and skin disassociation. Streuli et al. (1991) *J. Cell. Biol.* 115:1383–1395; Hiria et al. (1992) *Cell* 69:471481. After rinsing three times in media, the cells can be plated at $10^4$ cells/cm$^2$ in dishes coated by matrix laid down by human epidermoid A-431 cells (ATCC). Kantengwa et al. (1997) *Exp. Cell. Res.* 237:394402. This matrix is similar to that produced by pancreatic cancers being rich in laminin 5 (Shimoyama et al. (1995) *Int. J Pancreatol.* 18:227–234; Tani et al. (1997) *Am. J. Pathol.* 151:1289–1302). Laminin 5-rich matrices have been shown to expansion of both fetal and adult human islet preparations but often with concurrent cell dedifferentiation. Otonkoski et al. (1994) *Diabetes* 43:1164–1166; Lefebvre et al. (1998) Diabetes 47:134–137. Primary duct cells grown on collagen I or Matrigel (rich in laminin 1) show differentiation. The medium will initially be that termed Hepatocyte Growth Medium (Block et al. (1996) *J. Cell. Biol.* 132:1133–1149) without dexamethasone. Dexamethasone has been shown to drive pancreatic duct cell line AR42J to exocrine phenotype (Mashima et al. (1996) *J. Clin. Invest.* 97:1647–1654) as well as down regulating PDX-1 expression (Sharma et al. (1997) *Mol. & Cell. Biol.* 17:2598–2604). HGF (10 ng/ml, R&D, MN) and EGF (20 ng/ml, Collaborative Research, Waltham, Mass.) can be added fresh with each media change. It was found in primary duct cell cultures that 10 ng/ml HGF resulted in 2 fold increase of BrdU incorporation and that 50 ng/ml did not increase it further. So, initially, a lower dose can be used than used with hepatocytes.

Initially monitoring of cell growth can be by visual assessment under phase microscope, followed by DNA content at alternative days after plating until confluence is reached. If confluence is not reached by 21 days, the components can be systematically tested for effectiveness. One of the first media components to delete experimentally can be galactose, since galactose inactivates the binding of the 67 kD non integrin laminin receptor and causes its loss from the cell surface. Privitera et al. (1998) *J. Biol. Chem.* 273:6319–6326. The presence of this laminin receptor has been correlated with the invasiveness of tumors and dedifferentiation. Van den Brule et al. (1994) *Biochem. Biophys. Res. Comm.* 201:388–393. Thus, the loss of this receptor may prevent rapid growth as well as initiate or maintain a differentiated state, and so galactose in the expansion media may be detrimental to expansion and dedifferentiation.

If further expansion is needed, KGF (Upstate Biotechnology) can be added since there is in vivo data showing stimulation of replication of duct cells by this factor and KGF would stimulate through a different receptor than the other factors used.

To demonstrate that most of the pancreatic cells have the ability to expand rather than just a few true stem cells that continually replicate, labeling of the cultured cells at day 2 can be performed and the cells followed over 14 days. This can be done by transducing the cultures at 48 hrs with a replication deficient retrovirus containing green fluorescent protein (GFP) under an LTR promoter. Media can be replaced with supernatant containing $5 \times 10^5$ units per ml and polyprene (2 ug/ml)overnight. After 14–16 hrs (overnight) the cells can then be washed and the optimal growth media replaced. If the exposure to virus/polybrene has adverse effects on the cell survival, it can be triturated to the dose and time of exposure. It is expected that scattered single GFP positive cells will be seen initially (within a few hours) but with time (and expansion) only clusters of GFP positive cells will be seen. The advantage of using GFP is that the cells can be monitored over time without fixation. For evidence of clonal expansion, increased numbers of clusters of GFP+ cells need to be found.

Monitoring Changes in Gene Expression During this Expansion:

Once the conditions are optimized for growth, total RNA can be extracted at zero time, 1, 2, 6, 10, and 14 days using Ultaaspec (Biotecx Laboratories). These samples can then be probed by multiplex RT-PCR for: islet hormones and amylase to rule out differentiation; GLUT 2, Pref-1 both found in early embryonic duct markers and beta cells; LDH for differentiated duct marker (mature adult ducts strongly express lactose dehydrogenase (LDH) at both the gene and protein level but that proliferating ducts express less and normal islets almost none). Additionally immunostaining and/or Western blot analysis can be done at least for IPF-1 (PDX-1) since it is suggested IPF-1 (PDX-1) is regulated at least in the ducts by post transcriptional control. Similar patterns of expression are likely as in the in vivo experiments described previously for those genes that are affected by replication and not cell-matrix or cell-cell interactions.

Additionally, genes that were found to change in the epithelial cells in vivo (e.g., growth factors, their receptors, integrin subunits, Pref-1, u-PA) can be screened by RT-PCR in this system as the untreated controls in the following set of experiments.

The changes in duct gene expression seen the in vivo experiments described previously could result from intrinsic changes in the duct cells that occur with rapid replication or from extrinsic influence of cytokines, such as TGF-β and HGF which change in and around the ducts after Px. While both TGFβ and HGF affect the replication of primary ductal epithelium, with HGF doubling it, and TGFβ reducing it 10 fold, each probably has additional effects on the duct cells.

The expanded duct cells provide a system to dissect the changes in phenotypic expression intrinsic to rapid replication from those induced by the cytokines seen in vivo after Px. It is possible that TGF-β induces changes in the duct epithelium beyond its effect on replication and that these changes are in the expression of integrins, laminins as well as HGF, u-PA and its receptor, and TGFβ itself. To do this, the expanded duct cells can be treated with TGFβ (R&D) with different doses (O-50 ng/ml) for 24 hrs or at one dose for varying times (0, 6 hour, 24 hours and 48 hours). Another control dish can be treated with 100 ng/ml soluble TGF receptor II (Biogen). This reagent blocks the action of TGF-β and so the effects of endogenous TGF-β can be removed. In the first experiments, RNA can be extracted and screened by RT-PCR for the integrin a subunits and laminins found in vivo in the earlier experiments, u-PA and its receptor, TGF-β and HGF. For those genes whose expression is influenced by the cytokine, protein expression can be analyzed by immunostaining and/or Western blots on additional dishes of treated cells. If u-PA or HGF are increased, another control can be added, that of treatment with the neutralizing antibody to u-PA (American Diagnostica) and/or HGF (R&D) to show which protein is the actual effector. A similar set of experiments can be done for HGF treated expanded cells using a similar protocol and analysis to test whether HGF has direct effects on the ductal phenotype. These sets of experiments should allow understanding of the mechanism of the changes in the ductal phenotype that is seen in vivo. Based on data from functional or actual TGF-β (Crawford et al. (1998) Cell 93:1159–1170; Bottinger et al. (1997) EMBO J. 16:2621–2633), in null mice it would be expect that continued TGF-β is essential for exocrine differentiation from ducts rather than for endocrine differentiation but that it is necessary in the overall regulation of pancreatic regeneration by being part of a complex regulatory network. Understanding the regulation of both cell matrix and cell adhesion genes in this system may eventually allow targeted modulation.

Using these expanded duct cultures to test factors to stimulate differentiation to pancreatic is reached. One advantage of generating such an in vitro system is to be able to analyze and manipulate the process of differentiation in vitro. Several approaches to induce differentiation that have been used in other systems can be tested for effectiveness in the duct cells, and their effects can be assessed by cell morphology and multiplex RT-PCR analysis of islet hormones and amylase. Immunostaining for these phenotype markers would be a second tier measurement of phenotypic change to determine what proportion, if any, of the cells have differentiated. In each of the following sets of experiments, induction of islet hormone and/or amylase mRNA leads to further analysis of the time frame of induction and the mechanism involved. It is likely that the sequence of events (changes in profiles of expressed integrin subunits, their location along the cell membrane and their phosphorylation state, expression of Pref-1, etc.) follows the reverse pattern of dedifferentiation. However, it is realized that the two processes may not be mirror images.

Initially, the ability of these cells to differentiate can be tested in vivo by making aggregates and transplanting the equivalent of 10,000 cells under the kidney capsule of nude mice. For transplantation, animals can be anesthetized with Metofane and have a lumbar incision through which the left kidney is exteriorized. The aggregates are quickly inserted under the kidney capsule, the kidney repositioned and the incision stapled close. After 2 weeks, the animals are overdosed with anesthesia and the grafts are excised for ultrastructural analysis to determine the cellular phenotypes present. It is likely that both duct and islet phenotypes will be seen.

This transplantation experiment can test if these cells retain the ability to differentiate into mature ducts and islets.

These cells can also be studied in vitro with changes in the culture conditions as detailed following, to extract RNA at specified times and to analyze the RNA using multiplex RT-PCR for the spectrum of genes determined to be part of the differentiation pathway to islet, exocrine or duct.

An in vitro increase in calcium concentration induces differentiation in epidermal cells by blocking the α3β1 integrin binding to epiligrin/laminin 5. Weitzman et al. (1993) J. Biol. Chem. 268:865–8657. In addition, there is intercellular accumulation of both α3β1 and α2β1 integrins and increased cell-cell adhesion. To test this approach, duct cells can be expanded in 12 well plates by the protocol devised above. After some dedifferentiation has occurred (determined empirically above), the media is changed to the basal media without growth factors (HGF, EGF, KGF, etc.) but with 1 mM Ca++, and the cells can then be followed for variable times (2 hours, 12 hours, 1 day, 3 days) before RNA extraction. One visible change may be that the cells lift off the matrix and even reaggregate. If so, the media can be centrifuged to retrieve cells before extracting RNA. Such reaggregation itself may be beneficial based on evidence with fetal human pancreatic cells.

It can also be tested whether laminin 1 or Matrigel can drive these cells to differentiation. Expanded hepatocytes redifferentiate when Matrigel gels were made by adding 50 ul of Matrigel solution into 0.5 ml of medium on top of the attached cells, forming a gel over the attached cells. A protocol similar to that described for Ca++ can be used to assess the effect of added matrix. Since Matrigel itself is composed of laminin 1, laminin 5, type IV collagen and heparin sulfate proteoglycan, laminin 1 can be used alone in parallel experiments.

It can also be tested whether betacellulin by itself or with exendin-4 can drive differentiation of these cells. It has been reported that betacellulin has differentiative effects on AR42J cells. Ishiyama et al. (1998) Diabetologia 41:623–628; Mashima et al. (1996) Endocrinol. 137:3969–3976. Additionally, it has been found in a islet precursor cell line that betacellulin exendin-4 (0.1 (1 nM) ng/and ml, Peninsula), alone or together, activate the promoter by 4 days of treatment. Based on these data, it appears that these factors drive differentiation of the expanded duct cells to some degree. RNA extraction can be done at 4 days after introduction of betacellulin exendin, and gene expression can be examined as described above.

In addition, it can be determined whether the omission of galactose from the expansion media, drives an expanded population to differentiation. Galactose inactivates the 67 kD laminin receptor, a protein putatively accounting for a dedifferentiated state and invasiveness of tumors. Priviteria et al. (1998) J. Biol. Chem. 273:6319–6326. To test if the shedding of this non-integrin laminin receptor will have an effect on the differentiative state, dishes with near confluent cells can have media changed to have galactose (2g/L). RNA will be extracted at 24 and 48 hrs and analyzed.

The expression of TGFβ during the regeneration following partial pancreatectomy showed that TGFβ is an autocrine regulator of pancreatic duct proliferation. In vitro studies confirmed that that TGFβ was an inhibitor of ductal proliferation but did not induce expression of islet hormones (i.e., differentiation to islet tissue) in the cultured duct cells. Recently mice null for thrombospondin-1 (the major in vivo activator of latent TGF-β) or null for TGF-β1 were shown to have the pancreatic phenotype of masses of ductules, islets but little exocrine tissue, suggesting that TGFβ not only regulates duct proliferation but also the differentiation into exocrine tissue. Studies on another transgenic mouse (Bottinger et al. (1997) EMBO J. 16:2621–2633), one with an inducible dominant-negative mutant TGFβ type II receptor, showed that TGF-β inhibits acinar growth and is necessary for the maintenance of the differentiated pancreatic exocrine phenotype. A soluble rabbit TGFβ type II receptor available from Biogen has been used in rats in vivo (liver regeneration after bile duct ligation) and in vitro and effectively blocks TGF-β action. Since it was shown that TGF-β is an autocrine regulator of ductal proliferation, blocking its action in vivo may allow continued duct proliferation.

Using soluble TGF-β receptor in vivo is likely to result in a greater expansion of ductal epithelium and, hence, an increase in the facultative stem cells available for differentiation. To test this hypothesis, a 90% pancreatectomy can be performed on 4–5 week old male Sprague Dawley rats. This degree of pancreatectomy results in a mild to moderate hyperglycemia (plasma glucose levels being 190–250 mg/dl Px vs. 150–160 sham Px) by 3–4 days post surgery. In the first experiments, soluble TGF-β receptor (1 mg/kg in sterile, endotoxin free PBS) can be injected 24 hours after Px intravenously through the tail vein, and this treatment can be repeated every other day for 7 days. This dosage in rats has been used for 3–4 weeks without undue effects (e.g., weight loss). There is little immuno-detectable TGF-β1 around the larger ducts at 1 or 2 days after Px but it reappears at 3 days. Animals can be weighed and bled at weekly intervals. At 7 days, under Nembutal overdose anesthesia, the pancreas can be excised, weighed, fixed in 4% (para) formaldehyde and embedded in paraffin. Sections can be immunostained for islet hormones and/or PDX-1 using immunoperoxidase techniques. In untreated animals, it is found that by 7 days less than 1% of the pancreatic remnant is still composed of areas of small ductules, called foci of regeneration, but that the weight of the remnant has increased 2.5 fold. Initially sections can be read to see if there has been a substantial increase in the volume of these foci. If subjectively there is an increase, focal areas can be quantitated and islets using point counting morphometrics and PDX-1 protein expression can be looked for in these ductules. PDX-1 protein can serve as a marker of dedifferentiated ducts. Since TGF-β may modify both cell matrix composition and cell integrin expression, it is a good candidate for influencing the redifferentiation of the expanded duct cells. Therefore, PDX-1 expression is expected to be maintained in the ducts after this treatment. If however, there is no increase in focal areas or no PDX-1 staining in ductules, analysis can be performed to determine if there had been equal or greater growth of the remnant than in untreated. A greater remnant weight could, based on the TGF-β mutant receptor transgenic mouse, result from the existing exocrine tissue having proliferated more than the usual enhancement after Px surgery and so an increase in foci may be not be apparent even though it may have occurred. The morphometric data can help distinguish between these alternatives since the absolute volume of islet and ductular regions can be calculated. Since the soluble receptor is a fusion of the extracellular domain of the TGF-β receptor and the Fc region of human IgG, it can be verified that this receptor has reached the target tissue (pancreas) by immunostaining using an anti human IgG as primary antibody.

If there has been an increase in ductal expansion after blocking of TGF-β action, it can be determined if these duct cells differentiate once the soluble receptor injections are stopped. To test if there can be differentiation after the end of treatment with soluble TGF receptor, animals can be first treated with the reagent for 7 days and then followed for the subsequent 21 days. Body weight and plasma glucose can be measured weekly after Px and compared to untreated Px animals. Decreasing glucose values is suggestive of enhanced beta cell mass if the weight gain is comparable. At 21 days after stopping treatment (4 weeks after Px), the animals can be sacrificed and the pancreas taken for morphological assessment. The fate of the expanded ductules can be assessed again initially subjectively and then morphometrically, if needed, to determine whether there has been differentiation into islets or exocrine. It is entirely possible based on the above mentioned transgenic and null mice that the ductules differentiate mainly to exocrine cells, in fact this is the normal pattern in which the islets are only 1–2% of the volume of pancreas.

If mainly exocrine differentiation or a maintained ductal mass without further differentiation are found, the experiment can be repeated but start daily injections of exendin-4 (0.1 nmol/kg body weight IP) at day 5 and continue for 14 days. The starting time of the exendin treatment is dependent on the finding above of PDX-1 protein expression in the expanded ductules at 7 days. The exendin treatment should be started at a time that PDX-1 is still expressed in the ductules since these PDX-1+cells are likely the precursor cells. These animals can be sacrificed at Px+4 weeks as before. Their body weight, plasma glucose levels, and pancreatic morphology can then be compared with the above experiment. It is expected that a drop in plasma glucose levels and an increased beta cell mass will be seen. If this dual treatment can markedly enhance the beta cell mass by driving the differentiation of the expanded duct cells toward beta cells, finding a noninvasive method of stimulating ductal proliferation to be used in a similar protocol can be pursued. Such a non-invasive way to increase beta cell mass would open new directions for beta cell replacement.

All patents and other references cited herein are hereby incorporated by reference.

What is claimed:

1. A method of obtaining pancreatic islet cells, the method comprising:
   providing differentiated pancreatic duct or exocrine cells substantially free of islet cells,
   allowing said differentiated duct or exocrine cells to proliferate to form a population of dedifferentiated pancreatic cells;
   adding a component of extracellular matrix (ECM) to the population of dedifferentiated pancreatic cells; and
   growing the cells in the presence of the component of ECM for a time sufficient for the dedifferentiated cells to express insulin, thereby obtaining pancreatic islet cells.

2. The method of claim 1, wherein the population of dedifferentiated pancreatic cells has been cultured until at least about 70% confluency before adding a component of the extracellular matrix.

3. The method of claim 1, wherein the dedifferentiated pancreatic cells express cytokeratin.

4. The method of claim 1, wherein the component of extracellular matrix is laminin.

5. The method of claim 1, wherein the component of extracellular matrix is a basement membrane derived substance.

6. The method of claim 5, wherein the basement membrane is laid down by an Engelbreth-Holm-Swarm tumor cell.

7. The method of claim 1, wherein the component of extracellular matrix is added by overlaying the population of dedifferentiated cells.

8. The method of claim 1, wherein at least a portion of the pancreatic islet cells form cultivated islet buds.

9. The method of claim 8, wherein the cultivated islet buds comprise hormone positive islet cells.

10. The method of claim 8, wherein the cultivated islet cells express increased levels of insulin expression as compared to the dedifferentiated cells.

11. The method of claim 1, wherein the pancreatic islet cells have the ability to secrete insulin in response to glucose.

12. A method of obtaining pancreatic islet cells, the method comprising:
(a) obtaining a population of adult or differentiated pancreatic cells substantially free of islet cells,
(b) allowing the adult or differentiated pancreatic cells to proliferate to form a population of dedifferentiated pancreatic cells;
(c) adding a component of extracellular matrix (ECM) to the population of dedifferentiated pancreatic cells; and
(d) growing the cells in the presence of the component of ECM for a time sufficient for the dedifferentiated cells to express insulin, thereby obtaining pancreatic islet cells.

13. The method of claim 12, wherein the population of adult or differentiated pancreatic cells substantially free of islet cells is obtained from cells remaining after islet isolation from a pancreatic tissue.

14. The method of claim 12, wherein the population of adult or differentiated pancreatic cells substantially free of islet cells is selected based on their ability to adhere to a container.

15. The method of claim 12, wherein the dedifferentiated pancreatic cells express cytokeratin.

16. The method of claim 12, wherein the component of extracellular matrix is laminin.

17. The method of claim 12, wherein the component of extracellular matrix is added by overlaying the population of dedifferentiated cells.

18. The method of claim 12, wherein at least a portion of the pancreatic islet cells form cultivated islet buds.

19. The method of claim 18, wherein the cultivated islet buds comprises hormone positive islet cells.

20. The method of claim 12, wherein the pancreatic islet cells have the ability to secrete insulin in response to glucose.

21. The method of claim 12, wherein in step (b) an agent that promotes expansion is added to the adult or differentiated pancreatic cells.

22. The method of claim 21, wherein the agent is a growth factor or a combination of growth factors.

23. The method of claim 22, wherein the growth factor is selected from the group consisting of: keratinocyte growth factor, epidermal growth factor, transforming growth factor-α, hepatocyte growth factor, and combinations thereof.

24. The method of claim 23, wherein the growth factor is keratinocyte growth factor.

25. The method of claim 12, wherein in step (b) the adult or differentiated pancreatic cells are placed on a substrate in a glucose-containing media.

26. The method of claim 12, wherein the population of adult or differentiated pancreatic cells is cultured until at least about 70% confluency before adding the component of extracellular matrix.

27. The method of claim 1, or 12, wherein the component of extracellular matrix is collagen.

28. The method of claim 1, or 12, wherein the component of extracellular matrix is entactin.

29. The method of claim 1, or 12, wherein the component of extracellular matrix is heparin sulfate proteoglycan.

30. The method of claim 1, or 12, wherein the component of extracellular matrix is nidogen.

31. The method of claim 1, wherein the proliferation is characterized by expression of IPF-1.

32. The method of claim 1, wherein the proliferation is characterized by expression of PDX-1.

33. The method of claim 1, wherein the proliferation is characterized by expression of Pref-1.

34. The method of claim 12, wherein the proliferation is characterized by expression of IPF-1.

35. The method of claim 12, wherein the proliferation is characterized by expression of PDX-1.

36. The method of claim 12, wherein the proliferation is characterized by expression of Pref-1.

* * * * *